United States Patent [19]
Tsuchiya

[11] Patent Number: 5,441,054
[45] Date of Patent: Aug. 15, 1995

[54] APPARATUS FOR MEASURING ABSORPTION INFORMATION IN SCATTERING MEDIUM AND METHOD THEREFOR

[75] Inventor: Yutaka Tsuchiya, Hamamatsu, Japan
[73] Assignee: Hamamatsu Photonics K.K., Hamamatsu, Japan
[21] Appl. No.: 92,996
[22] Filed: Jul. 19, 1993

[30] Foreign Application Priority Data

Jul. 20, 1992 [JP] Japan .................................. 4-192370

[51] Int. Cl.⁶ .............................................. A61B 6/00
[52] U.S. Cl. .................................. 128/665; 128/664; 128/633; 250/341.1; 356/39
[58] Field of Search ......................... 128/664, 665, 633; 356/432, 433, 39; 250/339.12, 341

[56] References Cited

U.S. PATENT DOCUMENTS

| | | | |
|---|---|---|---|
| 4,515,165 | 5/1985 | Carroll | 128/665 |
| 4,767,928 | 8/1988 | Nelson et al. | 128/665 |
| 4,945,239 | 7/1990 | Wist et al. | 128/665 |
| 4,948,974 | 8/1990 | Nelson et al. | 128/664 |
| 4,972,331 | 11/1990 | Chance . | |
| 5,099,123 | 3/1992 | Harjunmaa | 356/39 |
| 5,203,339 | 4/1993 | Knüttel et al. | 128/665 |
| 5,253,646 | 10/1993 | Delpy et al. | 128/665 |
| 5,293,210 | 3/1994 | Berndt | 356/39 |

OTHER PUBLICATIONS

Wang et al, "Ballistic Imaging of Biomedical Samples Using Picosecond Optical Kerr Gate", SPIE, vol. 1432, Time-Resolved Spectroscopy and Imaging of Tissues 1991, pp. 97–101.

Toida et al, "The First Demonstration of Laser Computed Tomography Achieved by Coherent Detection Imaging Method for Biomedical Applications", IEICE Transactions. vol. E 74, No. 6, Jun. 1991, pp. 1692–1694.

Toida et al, "Approach to Optical Computer Topography for Highly Scattering Biological Subjects Using an Optical Heterodyne Method", CLEO '90 Conf. Laser and Electro-Optics, 1990 Tech. Dig. Series, pp. 548–550.

Arridge et al, "Reconstruction Methods for Infra-Red Absorption Imaging", SPIE, vol. 1431, 1991, pp. 204–215.

(List continued on next page.)

*Primary Examiner*—Lee S. Cohen
*Assistant Examiner*—Brian L. Casler
*Attorney, Agent, or Firm*—Cushman Darby & Cushman

[57] ABSTRACT

Modulated light from a light source is incident on the surface of a scattering medium, and light passing through this scattering medium is externally detected. A signal of a predetermined frequency component is extracted from this detection signal to detect a photon density wave propagating in the scattering medium. A signal extracted to correspond to this photon density wave is compared with the signal of the predetermined frequency component constituting the original incident modulated light to detect a predetermined quantitatively measurable parameter such as a phase difference at a detection point. This parameter has a specific relationship with the absorption coefficient by an absorptive constituent in the scattering medium as being derived from the photon diffusion theory, so that the predetermined parameter is appropriately arithmetically processed to obtain various kinds of absorption information (including the linear integration value of the absorption coefficient in the scattering medium and the concentration of a specific material) associated with absorption in the scattering medium.

27 Claims, 20 Drawing Sheets

OTHER PUBLICATIONS

Oda et al, "Non-Invasive Hemoglobin Oxygenation Monitor and Computed Tomography by NIR Spectrophotometry", SPIE, vol. 1431 (1991), pp. 284-293.

Patterson et al, "Applications of Time-Resolved Light Scattering Measurements to Photodynamic Therapy Dosimetry", SPIE, vol. 1203 (1990), pp. 62-75.

Patterson et al, "Time Resolved Reflectance and Transmittance for the Non-Invasive Measurement of Tissue Optical Properties", Applied Optics, vol. 28, No. 12, 1989, pp. 2331-2336.

Sevick et al, "Time-Dependent Photon Migration Imaging", SPIE, vol. 1599, (1991), pp. 273-283.

Fishkin et al, "Diffusion of Intensity Modulated Near-Infrared Light in Turbid Media", SPIE, vol. 1431 (1991), pp. 122-135.

Sevick et al, "Quantitation of Time-and Frequency-Resolved Optical Spectra for the Determination of Tissue Oxygenation", Analytical Biochemistry, vol. 195, pp. 330-351 (1991).

Lakowicz et al, "Advances in Frequency-Domain Fluorometry; Gigahertz Instrumentation; Time-Dependent Photo Migration and Fluorescence Lifetime Imaging", SPIE, vol. 1599, (1991), pp. 227-243.

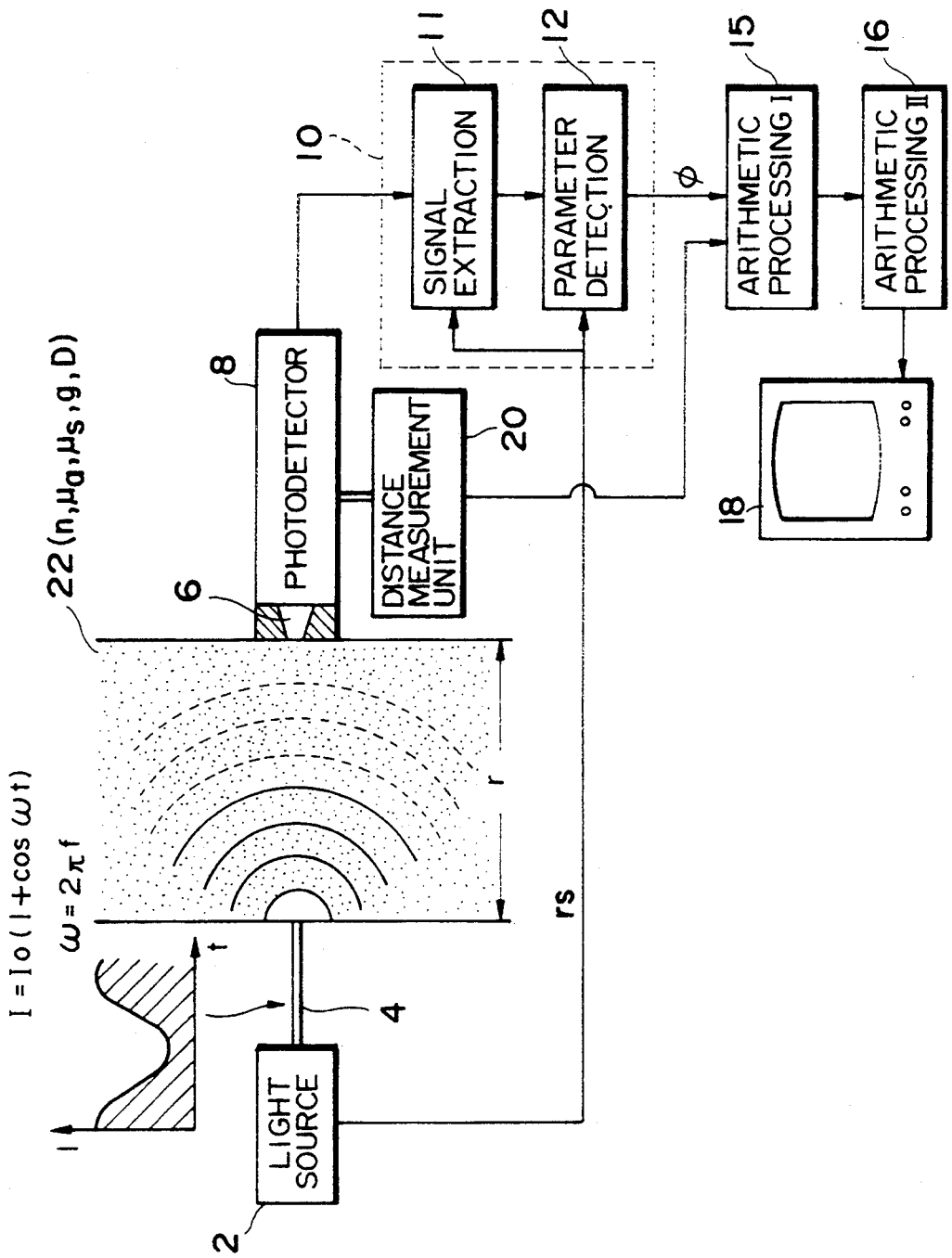

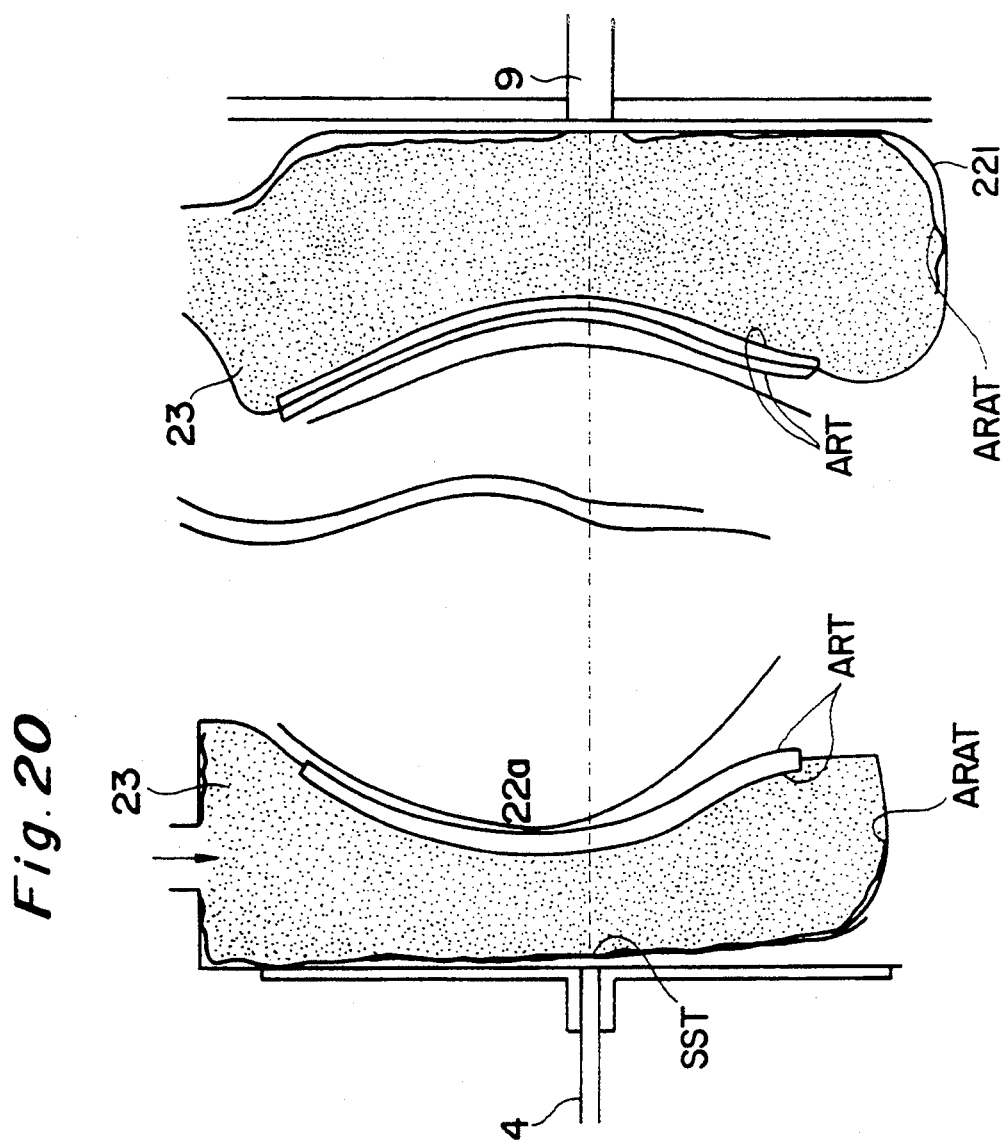

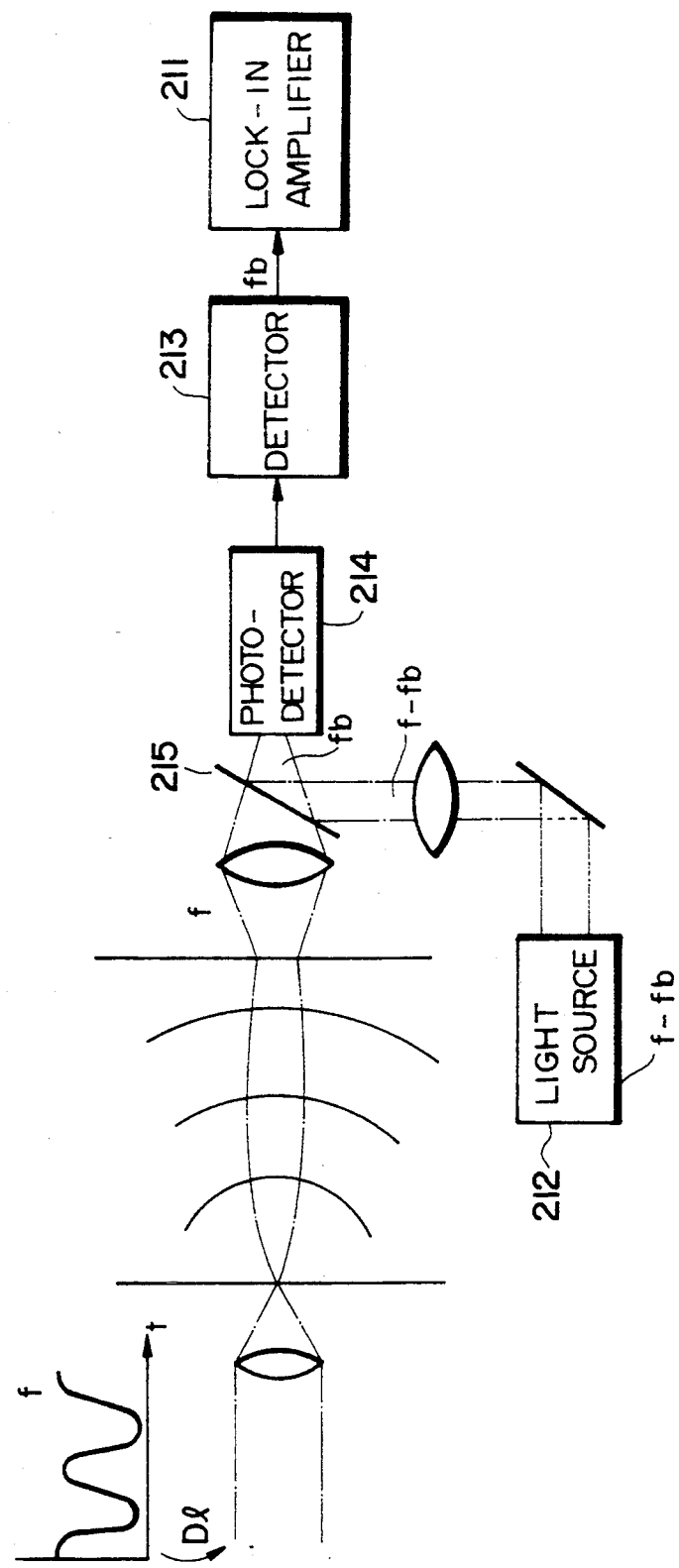

APPARATUS FOR MEASURING ABSORPTION INFORMATION IN SCATTERING MEDIUM AND METHOD THEREFOR

BACKGROUND OF THE INVENTION

1. Field of the Invention

The present invention relates to an apparatus and method for performing measurement of information associated with an absorptive constituent in a scattering medium such as a living body by utilizing light and, more particularly, to an apparatus for measuring absorption information in the scattering medium, capable of measuring the concentration of a specific absorptive constituent in the scattering medium, its time change, its spatial distribution, and the like, and improving measurement precision.

2. Related Background Art

Measurement or imaging in a living body using light is advantageously non-invasive and allows analysis of internal components using a spectrum as an optical characteristic inherent to a given material. However, a living body is a typical scattering medium, and light is scattered and/or absorbed at random inside the living body. Excellent measurement and imaging as in X-ray or ultrasonic CT cannot be performed. That is, as most of the light components are greatly scattered inside the living body, straight light components are rarely present.

There are several reports and attempts in measurement and imaging of a scattering medium such as a living body using light. Main prior arts will be represented as references[1-12] at the end of this part (the number of each reference will be referred to with [x] hereinafter). Of these references, references[1-3] describe detection of straight light in a very small amount from scattered light. This detection has very poor light utilization because the amount of straight light is very small. In addition, measurement and imaging are time-consuming. This method is impossible to measure a large object such as a head. This method is not suitable for quantitative measurement of the concentration of absorptive constituents widespread in the living body and the concentration and absorption coefficients of localized absorptive constituents, although this quantitative measurement is one of the objects of the present invention.

Various kinds of references[4-11] utilizing scattered light are available. The reference[4] proposed by Delpy et al. describes image reconstruction such that scattered light outputs obtained upon incidence of pulsed light are detected at a plurality of positions, and an image representing internal absorptive constituents or an absorption distribution is reconstructed from these data. This method of image reconstruction is similar to that in X-ray CT. However, an image reconstruction algorithm for the scattered light is very complicated and is incomplete. A practical finding is not obtained yet.

Tamura et al.[5] propose a principle of an oxyhemoglobin concentration and a reduced or deoxygenated hemoglobin concentration in accordance with a change of absorbance optical density with respect to incident light components having three different wavelengths. Optical CT construction using this principle is also attempted. However, this method poses a lot of problems in terms of measurement precision because the length of an optical path upon a change in absorption coefficient is assumed to be constant. This problem is common to subsequent prior art methods and will also be described later.

References[6-8] are attempts for measuring internal absorption information by analyzing the time-resolved response upon the incidence of pulsed light to the medium. An output light signal upon incidence of the pulsed light on a scattering medium is temporally broadened by scattering and absorption constituents and has a long decay tail. Patterson et al[6] assume a model of uniform scattering medium to analytically obtain the light signal output. A waveform representing a time change in intensity of the optical output signal given by the formula defined by Patterson et al. matches a waveform obtained by an experiment using a scattering medium (e.g., a uniform medium) having a simple structure. According to Patterson et al., the absorption coefficient of absorptive constituents in the scattering medium is given by an incline (differential coefficient) obtained when the optical signal is sufficiently attenuated, i.e., when a sufficiently long period has elapsed. According to this method, however, since the optical signal corresponding to a portion subjected to absorption coefficient measurement must be sufficiently attenuated, the S/N ratio of the signal becomes low, and an error increases. Therefore it is difficult to use this method in practice. In addition, a long period of time must elapse until the optical signal is sufficiently attenuated, and the measurement time is inevitably prolonged.

To the contrary, Chance et al. propose a method[7] of obtaining an incline at an earlier timing and approximating an absorption coefficient with the incline value when the light intensity is not sufficiently attenuated. According to their proposal, an error in a simple scattering medium such as a uniform medium is about 10%. However, there is no guarantee to monotonously attenuate the above waveform in an actual living body having a complicated structure, and a DC light component increases by the scattered light. As a result, errors caused by the above phenomena are also added to further increase the errors. Also, errors caused by individual differences cannot be inevitably avoided, either.

The main reason why the problems for obtaining the absorptive constituent and an absorption coefficient in a scattering medium are complicated lies in that it is difficult to measure influences of the scattering and absorption coefficients separately, because the waveform of the scattered light output signal corresponding to the incident light pulse is deformed by scattering and absorption in the scattering medium, i.e., by the scattering and absorption coefficients. In other words, in the method of measuring the optical density, the optical density by its definition equalizes the scattering coefficient with the absorption coefficient as equivalent parameters. It is essentially difficult to separate the influences of the scattering and absorption coefficients and accurately obtain the influence of the absorption coefficient.

Sevick and Chance[8] calculated the average optical path length of detected output light components from the barycenter, i.e., the average delay time of the waveform of an output signal and confirm dependency of the average optical path length on the absorption coefficient. They also attempt to measure absorptive constituents localized inside the scattering medium from a change in average optical path length[8]. According to their experimental result, the average optical path length apparently depends on absorption. This indicates that the method[5] of Tamura et al. cannot measure the internal absorptive constituents accurately because the optical path length is assumed to be constant. The method of Sevick and Chance explicitly indicates that the concept of the average optical path length depending on absorption is introduced to allow measurement of absorption information in the scattering medium. However, the above average delay time can be obtained after the output signal waveform becomes apparent as a whole. For this reason, measurement of the average delay time must be performed until the output light signal having a long, gradually attenuated tail is sufficiently attenuated, thereby prolonging the measurement time. Since the output light signal is obtained by time-resolved measurement, the improvement of measurement precision of the average optical path length to improve measurement precision as a function of time undesirably causes a decrease in S/N ratio. Therefore, calculation precision of the average delay time, i.e., the barycenter has a limitation. Signal processing for obtaining the barycenter is complicated, and an apparatus for performing time-resolved measurement is generally complicated and bulky, resulting in an impractical application.

In contrast to the above prior arts, Gratton et al. propose a method[9] utilizing light modulated with a sinusoidal wave in imaging of the interior of a scattering medium. This method utilizes coherent propagation of a wave having a modulated frequency component in the scattering medium, as will be described in detail with reference to the operational principle of the present invention. According to their report[9], although a coherent wave propagating in the scattering medium is confirmed in their experiment, optical parameters of an actual sample do not match the theoretically calculated values. This study is still in the stage of fundamental study. Detailed findings and means for a method of obtaining absorption and scattering coefficients, a method of measuring a change in concentration of the absorptive constituents as a function of time, a method of imaging the interior of the scattering medium, and a method of obtaining a tomogram are not yet obtained.

Chance proposed a method and apparatus for determining the concentration of an absorptive constituent in a scattering medium utilizing modulated light in 1989 prior to the report of Gratton et al., and U.S. Pat. No. 4,972,331[10] of this method was issued to Chance in 1990. According to his patent, an output signal upon incidence of modulated light on the scattering medium is detected and compared with a reference waveform (e.g., an incident light waveform) to determine a quantitatively measurable parameter, and the concentration of the absorptive constituent is quantitatively measured. In this case, a phase difference quantitatively measured by the method disclosed in the Chance's patent is equivalent to the optical path length, i.e., a distance up to the barycenter of the waveform obtained by the time-resolved measurement method.

This patent also discloses a method and apparatus utilizing the principle of dual-wavelength spectroscopy, i.e., a method and apparatus for alternately switching modulated light components having different wavelengths. According to Chance's patent, however, no practical method except that logarithmic conversion of the phase difference is proportional to the concentration of the absorptive constituent or the absorption coefficient is described about a relationship between optical parameters (e.g., the scattering coefficient of the scattering constituent in the scattering medium, the absorption coefficient of the absorptive constituent thereof, and the concentrations of the scattering and absorptive constituents) and the determined parameters (time, frequency, and phase). According to the analysis, examinations, and experimental results of the present inventor, to be described in detail later, however, the logarithmic conversion of the phase difference is not proportional to the concentration of the absorptive constituent or the absorption coefficient.

Judging form the above description, it is essentially impossible for the description of the Chance's patent to quantitatively measure the absorption coefficient of the absorptive constituent and its concentration.

The present invention does not utilize the relationship described by Chance. Since the present invention does not utilize the absorbance optical density method, the optical path length is not utilized.

In Chance's patent, any specific region through which light used for measurement pass through the scattering medium is not taken into consideration. That is, the average value of light components passing through the entire area of the scattering medium is taken into consideration. For this reason, measurement of absorptive constituents localized inside the scattering medium is not examined, as a matter of course.

Therefor, according to chance's patent, it is also impossible to measure the spatial distribution of the absorptive constituent which is inevitable in imaging and measurement of the interior of the scattering medium. In conclusion, according to Chance's patent, it is impossible to quantitatively measure the absorption coefficient and concentration of the absorptive constituent of a specific portion in the scattering medium, measure them with a change in time, and measure the spatial distribution of the absorptive constituent at all. In addition, it is also impossible to image the above constituents and form a tomogram, either.

In recent years, Sevick and Chance[11] have made experiments to systematically examine and analyze the parameters obtained in the time-resolved measurement method and a method (they call this method a frequency-resolved measurement method) utilizing the modulated light, and have discussed the relationship between these parameters, including analysis results obtained by other researchers to verify their analysis results[11]. Most of the major conventional methods for measuring absorption information in the scattering medium are examined in this report, which is very convenient for us.

This report mainly describes detailed conventional applications of the time-resolved measurement method. The following method is described in detail. That is, a method to obtain parameters such as an average optical path length and an absorption coefficient from an output light signal obtained by the time-resolved measurement. And then by using these parameters, the concentration and absorption coefficient of the absorptive constituent of the scattering medium, the degree of saturation of hemoglobin (concentration of oxyhemoglobins with respect to the total amount of oxyhemoglobins and reduced hemoglobins), and the like are obtained. In this method, the barycenter (i.e. average delay time) of the output light signal waveform is obtained and multiplied with a light speed in the scattering medium to obtain the average optical path length.

A relationship between the parameters obtained by the time-resolved and frequency-resolved measurement methods is also clarified. For example, when the modulation frequency is low, the phase difference obtained by the frequency-resolved measurement method is found to be proportional to the average optical path length obtained by the time-resolved measurement method. As described above, according to the report of Sevick and Chance, the detailed method of obtaining the absorption information such as the concentration and absorption coefficient of the absorptive constituent of the scattering medium, the degree of saturation of hemoglobins, and the like using the optical path length is disclosed.

This measurement method has a disadvantage in that information associated with absorption is obtained from the time-resolved waveform of the output light signal. As previously described, since the measurement parameter for obtaining the absorption coefficients is the average delay time, the measurement precision is not essentially improved. The signal processing is considerably complicated, the signal processing time is prolonged, and the resultant apparatus becomes considerably bulky.

Lakowicz et al.[12] has reported an attempt of utilizing a phase modulation technique developed to measure an attenuation curve of laser-excited fluorescence in imaging of the scattering medium. This is a simple imaging technique. No consideration is made on quantitative measurement of the absorption coefficient and concentration of the absorptive constituent.

It is an object of the present invention to provide an apparatus for measuring absorption information in a scattering medium, capable of greatly improve the limitations of the method[10] proposed by Chance and the method[11] reported by Sevick and Chance, obtaining an image or tomogram representing the distribution of the absorptive constituent in the scattering medium, and quantitatively measuring the absorptive constituents in the image and tomogram, and a method therefor.

This object can be achieved by introduction of the concept of a photon density wave propagating in a scattering medium, a new finding of a relationship between quantitatively measurable parameters such as time, frequency, phase, and amplitude with respect to the photon density wave, and optical parameters such as the scattering coefficient of a scattering constituent in the scattering medium, the absorption coefficient of an absorptive constituent therein, and their concentrations, and a new and improved method of eliminating the influences of scattering from the measured data described above to accurately measure only the influence of absorption and/or perform signal processing.

Part of the basic principle utilized in the present invention is excluded from the examination and analysis range in A1.2 (pp. 348) of the report[11] of Sevick and Chance because this method makes it impossible to perform measurement due to an excessively low S/N ratio.

References

1) L. Wang, Y. Liu, P. P. Ho, and R. R. Alfano: Ballistic images of Biomedical samples using picosecond optical Kerr gate, Proc. SPIE, Vol. 1431, pp. 97–101 (1991)

2) M. Toida, T. Ichimura, and H. Inaba: The first demonstration of laser computed tomography achieved by coherent detection imaging method for biological applications, IECE Trans., Vol. E74, No. 6, pp. 1692–1694 (1991)

3) M. Toida, T. Ichimura, and H. Inaba: Approach to optical computer tomography for highly scattering biological subjects using an optical heterodyne method, CLEO '90, Conf. Laser and Electro-Optics, 1990 Tech. Dig. Series, pp. 548–550 (1990)

4) S. R. Arridge, P. van der Zee, M. Cope, and D. T. Delpy: Reconstruction methods for infra-red absorption imaging, Proc. SPIE, Vol. 1431, pp. 204–215 (1991)

5) I. Oda, Y. Ito, H. Eda, T. Tamura, T. Takeda, R. Abumi, K. Nagai, H. Nakagawa, and M. Tamura: Non-invasive hemoglobin oxygenation monitor and computed tomography by NIR spectrophotometry, Proc. SPIE, Vol. 1431, pp. 284–293 (1991)

6) M. S. Patterson, J. D. Moulton, B. C. Wilson, and B. Chance: Application of time-resolved light scattering measurements to photodynamic therapy dosimetry, Proc. SPIE, Vol. 1203, pp. 62–75 (1990)

7) M. S. Patterson, B. Chance, and B. C. Wilson: Time resolved reflectance and transmittance for the non-invasive measurement of tissue optical properties, Applied Optics, Vol. 28, No. 12, pp. 2331–2336 (1989)

8) E. M. Sevick, N. G. Wang, and B. Chance: Time-dependent photon imaging, Proc. SPIE, Vol 1599, pp. 273–283 (1991)

9) J. Fishkin, E. Gratton, M. J. vande Yen, and W. W. Mantulin: Diffusion of intensity modulated near-infrared light in turbid media, Proc. SPIE, Vol. 1431, pp. 122–135 (1991)

10) U.S. Pat. No. 4,972,331 (the corresponding Japanese patent is Japanese Patent Laid-Open No. 2-234048)

11) E. M. Sevick, B. Chance, J. Leigh, S. Nioka, and M. Maris: Quantitation of time and frequency-resolved optical spectra for determination of tissue oxygenation, Anal. Biochem., Vol. 195, pp. 330–351 (1991)

12) J. R. Lacowicz, L. Gryczynski, H. Szmacinski, and K. Nowaczyk: Advances in frequency-domain fluorometry; Giga Heltz instrumentation; Time-dependent photo migration and fluorescence life time imaging, Proc. SPIE, Vol. 1599, pp. 227–243 (1991)

SUMMARY OF THE INVENTION

In order to solve the above problems, an apparatus for measuring absorption information in a scattering medium according to the present invention comprises (a) light-emitting means for emitting modulated light of light having a predetermined wavelength, (b) light-incident means for forming the modulated light having the predetermined wavelength into a spot and causing the spot to be incident on the scattering medium, (c) photodetecting means for photodetecting the modulated light, changed during propagation in the scattering medium, through an opening located near an outer surface of the scattering medium, (d) signal extracting means for extracting a signal of one predetermined frequency component constituting the modulated light from signals photodetected by the photodetecting means, (e) parameter detecting means for comparing the signal extracted by the signal extracting means with the signal of the predetermined frequency component of the modulated light to be incident on the scattering medium and detecting a predetermined parameter associated with propagation of a photon density wave having the predetermined frequency component in the scattering medium and absorption of the light of the predetermined wavelength constituting the photon density wave having the predetermined frequency component, (f) first arithmetic processing means for calculating first absorption information associated with an absorptive constituent in the scattering medium, utilizing a relationship between the predetermined parameter and an absorption coefficient obtained when the photon density wave having the predetermined frequency component propagates in the scattering medium, and (g) second arithmetic processing means for calculating second absorption information associated with the absorption coefficient in the scattering medium, on the basis of a plurality of first absorption information obtained by the first arithmetic processing means.

A method of measuring absorption information in a scattering medium according to the present invention comprises (a) the first step of emitting modulated light of light having a predetermined wavelength, (b) the second step of forming the modulated light having the predetermined wavelength into a spot and causing the spot to be incident on the scattering medium, (c) the third step of photodetecting the modulated light, changed during propagation in the scattering medium, through an opening located near an outer surface of the scattering medium, (d) the fourth step of extracting a signal of one predetermined frequency component constituting the modulated light from signals photodetected in the third step, (e) the fifth step of comparing the signal extracted in the fourth step with the signal of the predetermined frequency component of the modulated light to be incident on the scattering medium and detecting a predetermined parameter associated with propagation of a photon density wave having the predetermined frequency component in the scattering medium and absorption of the light of the predetermined wavelength constituting the photon density wave having the predetermined frequency component, (f) the sixth step of calculating first absorption information associated with an absorptive constituent in the scattering medium, utilizing a relationship between the predetermined parameter and an absorption coefficient obtained when the photon density wave having the predetermined frequency component propagates in the scattering medium, and (g) the seventh step of calculating second absorption information associated with the absorption coefficient in the scattering medium, on the basis of a plurality of first absorption information obtained in the sixth step.

According to the apparatus for measuring absorption information in the scattering medium and the method therefor of the present invention, when the spot-like modulated light is incident on the scattering medium such as a living body, the photon density wave having the specific frequency component constituting the modulated light coherently and regularly propagates in the scattering medium although the photon density wave having the specific frequency component is attenuated. The influence of the absorptive constituent is then obtained from the waveform of the photon density wave deformed by the scattering and absorptive constituents in the scattering medium. At this time, the above wave is assumed to concentrically spherically propagate through the scattering medium.

According to the apparatus and method of the present invention, the output light signal is photodetected by the photodetector or the like having the opening near the surface of the scattering medium on the side opposite to the source of the modulated light. The signal having the predetermined frequency component is extracted from the output light signal to detect the wave propagating in the scattering medium. The signal extracted as a component corresponding to this wave is compared with the signal having the predetermined frequency component of the incident original modulated light, to detect a quantitatively measurable predetermined parameter such as a phase difference $\Phi$ at the opening, i.e., at the point detecting the wave. This predetermined parameter has a certain relationship with an absorption coefficient $\mu_a$ by the absorptive constituent in the scattering medium. Then the predetermined parameter is properly arithmetically processed to obtain various kinds of information including the second absorption information; the linear integration value of the absorption coefficient in the scattering medium, the concentration of the specific material, and the like, associated with absorption in the scattering medium.

Assume that the predetermined parameter is the phase difference $\Phi$. In this case, from the analysis and experimental examinations of the present inventor, first absorption information $\Phi^2$ in the scattering medium is obtained on the basis of the new finding given such that the phase difference $\Phi$ is approximately in inverse proportion to the square root of the absorption coefficient $\mu_a$ by the absorptive constituent in the scattering medium. The second absorption information such as the degree of saturation of hemoglobins, the spatial distribution of the concentration of the specific material, and their changes as a function of time are arithmetically processed on the basis of the first absorption information $\Phi^2$.

According to the present invention, the absorption information thus obtained is regarded as the linear integration value on a path along a line in the scattering medium, which line is obtained by connecting the wave detection point and the position at which the spot-like modulated light is incident. Imaging in the scattering medium and reconstruction of a tomogram can be performed. In this case, a plurality of photodetectors can also be used.

In the apparatus for measuring the absorption information in the scattering medium, the second absorption information can also be immediately obtained without calculating the first absorption information in detail.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art form this detailed description.

BRIEF DESCRIPTION OF THE DRAWINGS

FIG. 13 is a diagram showing an arrangement of the first embodiment.

FIG. 20 is a view showing two interface vessels.

FIG. 21 is a diagram showing an arrangement of the sixth embodiment.

DETAILED DESCRIPTION OF THE PREFERRED EMBODIMENTS

1. Basic Principle of Measurement of Absorption Coefficient in Scattering Medium When sinusoidally modulated light at a KHz to GHz range is incident on a scattering medium such as a living body, the behavior of light in the medium can be derived from a photon diffusion theory. Near-infrared light may be used due to its transmittance for living tissue. In this case, a sinusoidal wave of angular frequency $\omega$ (frequency $f = \omega/2\pi$) accompanies attenuation, but coherently and regularly propagates in the scattering medium as a wave. This is theoretically and experimentally confirmed by Gratton et al.[9] This wave will be called the photon density wave, hereinafter.

The behavior of each photon constituting the above modulated light or photon density wave can be calculated by a computer. The behavior of the modulated light constituted by these photons can be analyzed, experimented, and examined in accordance with Monte Carlo calculation. The present inventor has made these analyses, experiments, and examinations to clarify the behavior of the modulated light or the photon density wave in the scattering medium.

When the analysis and experimental results of the present inventor are summarized, the followings can be derived.

Figure 1:
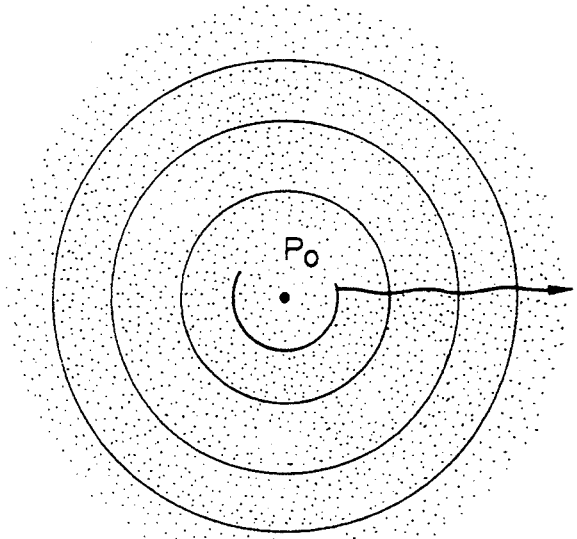
FIG. 1 is a view showing a state in which modulated light emitted from a point light source propagates in an infinite scattering medium as a wave of photon density.

A photon diffusion equation is generally solved under the assumption that a point light source Po is located inside an infinitely spread scattering medium, as shown in FIG. 1. In this case, the wave of the modulated frequency component ($f = \omega/2\pi$) coherently propagates in the scattering medium, and its wave front is concentrically spherical.

Figure 2:
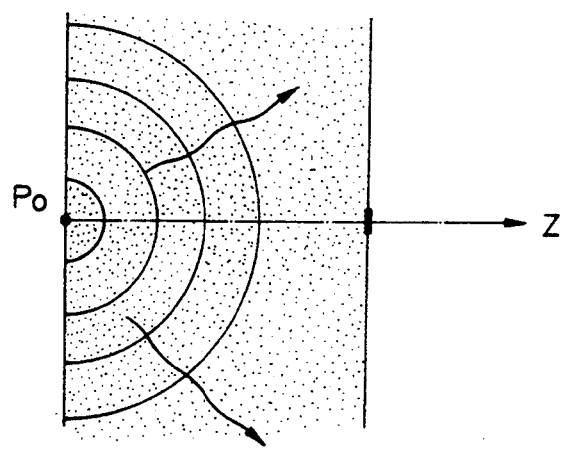
FIG. 2 is a view showing a scattering medium having a finite thickness and a photon density wave generated by a point light source located on the surface of the scattering medium.

To the contrary, in a practical apparatus, modulated light is incident on the outer surface of the scattering medium as in an imaging apparatus as one object of the present invention. In this case, the photon diffusion equation must satisfy a boundary condition on the surface of the scattering medium. This boundary condition is not to cause light or photon diffusion on the outer side of the scattering medium. FIG. 2 shows a state in which modulated light incident from a given point light source onto a slab-like scattering medium propagates in the scattering medium. In this case, at a location except for a location near the surface of the scattering medium, the wave for the modulated frequency component is regarded to coherently propagate like an almost spherical wave. Such a spherical wave is assumed in the following description.

Figure 3:
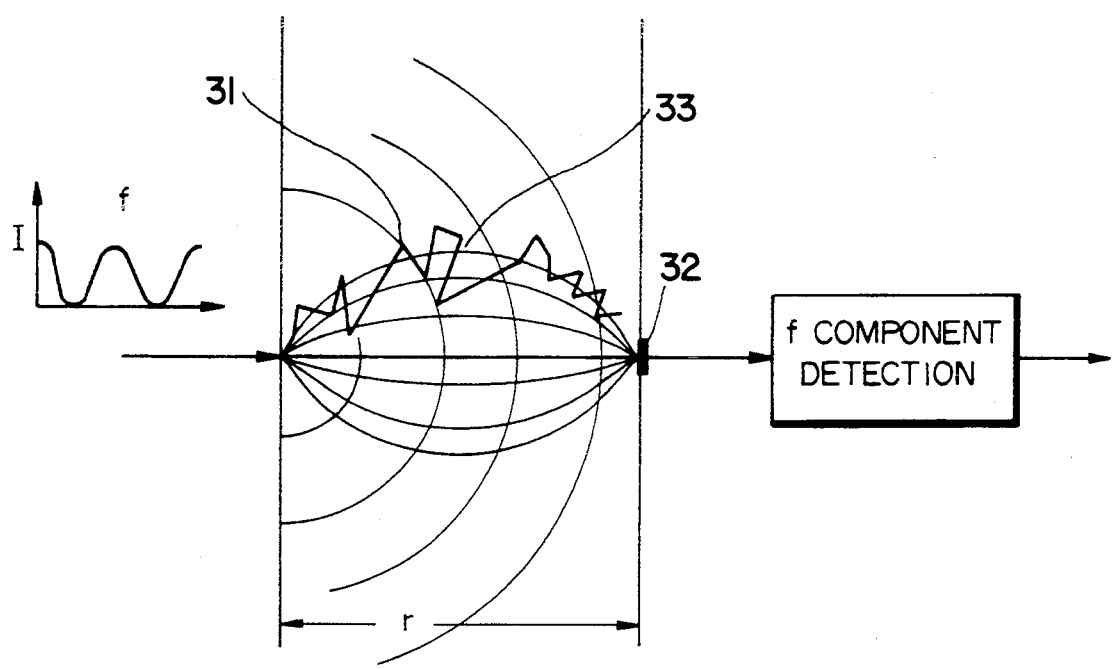
FIG. 3 is a view showing behavior of the photon density wave and photons constituting the wave in a scattering medium.

FIG. 3 shows a state in which spot-like modulated light is incident on the surface of the scattering medium 31, photons propagating through the scattering medium are detected by a photodetector 32 (usually having an input aperture), and a modulated frequency component signal is extracted from an output signal from the photodetector. In this case, of all the photons detected by the photodetector, photons constituting the wave of the modulated frequency component are regarded to roughly propagate along the spindle-shaped principal optical path 33 shown in FIG. 3. The spindle shape may have various diameters and may be a solid spindle shape. Reference numeral r in FIG. 3 denotes a distance from the light source to the photodetector (strictly speaking, the position at which light to be detected emerges from the scattering medium).

The detected absorption information utilizing the above wave reflects the absorption coefficient of the spindle-shaped portion between the light source and the photodetection point. If the absorption information is an integration value along the central line of the spindle shape, a tomogram can be reconstructed as in X-ray CT.

The above description has already been confirmed by Monte Carlo calculation by the present inventor. The above theory can be applied to any types of modulated light, if the frequency component of interest is contained. For example, repeated pulsed light has the sinusoidal wave components of the same frequency as the repetition frequency and an integer multiple of the repetition frequency. The above theory is applied to any one of the above sinusoidal wave components. The characteristics required for the modulated light are a stable repetition frequency and a stable repetition light intensity.

The behavior of the modulated light in the scattering medium is precisely examined on the basis of the above concept, and a relationship between the measurement parameters used in the present invention and the absorption coefficient of the absorptive constituent in the scattering medium to be measured will be described in detail on the basis of an example. For descriptive convenience, light modulated with a sinusoidal wave will be exemplified. The present invention is also applicable to repeated pulsed light and a repeated square wave light due to the same reason as described above. For the sake of descriptive simplicity, a solution derived from a photon diffusion equation is approximated in a pure form.

However, a result to be obtained can be applied to a case using a more strict solution.

2. Principle of Absorption Coefficient Measurement of Absorptive Constituent in Scattering Medium When spot-like light which is modulated with a sinusoidal wave of KHz to GHz and which tends to be transmitted through a scattering medium such as a living body is incident on the scattering medium, for example, the behavior of the spot-like light in the medium allows approximation of the following equation from the photon diffusion theory as follows.

Assume that a point light source is present within a uniform scattering medium. A light intensity $I(r,t)$ [photons/sec·mm$^2$] at a position spaced apart from the point light source by a distance $r$ at time $t$ is represented as follows. Note that a modulated wave which propagates through an infinitely spread scattering medium is assumed.

$$I(r,t) = (Sv/4\pi\alpha r) \times [\exp[-r(v\mu_a/\alpha)]^{\frac{1}{2}} + M\exp\{-rA(\omega)\cos B(\omega) - j[rA(\omega)\sin B(\omega) - \omega t + \epsilon]\}] \quad (1.1)$$

for $$A(\omega) = \{[(v\mu_a)^2 + \omega^2]/\alpha^2\}^{\frac{1}{2}} \quad (1.2)$$

$$B(\omega) = (\tfrac{1}{2})\tan^{-1}(\omega/v\mu_a) \quad (1.3)$$

$$\begin{aligned}D &= \alpha/v \\ &= 1/3\mu_{tr} \\ &= 1/\{3[\mu_a + (1-g)\mu_s]\}\end{aligned} \quad (1.4)$$

where
- S: the number of incident photons [photons/sec]
- M: the degree of modulation of the modulated light
- $\omega$: the angular frequency [rad/sec] of the modulated wave
- $\alpha$: the photon diffusion constant [mm$^2$/sec]
- $\epsilon$: the fixed phase term
- D: the photon diffusion coefficient [mm]
- v: the speed [mm/sec] of light in the scattering medium (the speed of light in a vacuum is given as c=vn where n is the refractive index)
- g: the average value of $\cos\theta$ with respect to the scattering angle $\theta$
- $\mu_{tr}$: the light attenuation coefficient [mm$^{-1}$]
- $\mu_a$: the absorption coefficient [mm$^{-1}$]
- $\mu_s$: the scattering coefficient [mm$^{-1}$]

At this time, a component $I_w(r,t)$ whose frequency is given as $f=\omega/2\pi$ is represented as follows. $j[rA(\omega)\sin B(\omega)-\omega t+\epsilon]\}$ \quad (1.5)

A phase difference $\Phi$ and an amplitude $I_p$ of the wave represented by equation (1.5) are approximated as follows. The following description will be made using these two approximated equations.

$$\Phi \approx rA(\omega)\sin B(\omega) \quad (1.6)$$

$$I_p \approx (Sv/4\pi\alpha r)M\exp[-rA(\omega)\cos B(\omega)] \quad (1.7)$$

As described above, the phase difference $\Phi$ represented by equation (1.6) is an approximated solution. A more strict phase difference contains a correction term, i.e., the second term as a function of the known modulation angular frequency $\omega$ and the unknown absorption coefficient $\mu_a$. In this case, this correction term is an almost constant small value and is neglected. To further improve the measurement precision in consideration of the above correction term, a more strict phase difference, i.e., a phase difference obtained by subtracting the correction value as a constant value from the phase difference $\Phi$ of equation (1.6) is used. Processing using this more strict phase difference is processing using the strict phase difference in place of the phase difference $\Phi$ of equation (1.6). In the following description, the more strict phase difference is assumed to be included in the phase difference $\Phi$.

According to the present invention, a living body is assumed as an object to be measured, so that the following values are assumed as the standard parameter values of the living body.

$$\begin{aligned}\mu_a &= 0.01 \text{ mm}^{-1} \\ \mu_s &= 3 \text{ mm}^{-1} \\ g &= 0.85 \\ (1-g)\mu_s &= 0.45 \text{ mm}^{-1} \\ n &= 1.33\end{aligned} \quad (1.8)$$

$$\begin{aligned}v &= 3 \times 10^{11}/1.33 \\ &= 2.26 \times 10^{11} \text{ mm/sec}\end{aligned} \quad (1.8)$$

$$\begin{aligned}v\mu_a &= 2.26 \times 10^9 \\ &= 2\pi \times 3.6 \times 10^8 \text{ sec}^{-1}\end{aligned} \quad (1.8)$$

Since $\mu_a << (1-g)\mu_s$, the following equation can be obtained.

$$A(\omega)=[3(1-g)\mu_s/v]^{\frac{1}{2}}[(v\mu_a)^2+\omega^2]^{\frac{1}{4}} \quad (1.9)$$

$$B(\omega)=(\tfrac{1}{2})\tan^{-1}(\omega/v\mu_a) \quad (1.10)$$

In this case, as $\omega$ takes various values with respect to $v\mu_a$, the range including the $\omega$ value is divided to perform analysis.

(1) $\omega << v\mu_a$

If the modulation frequency is given as f=100 MHz, the following equation is obtained:

$$\omega/v\mu_a=6.28\times 10^8/2.26\times 10^9=1/3.6$$

Assuming $f=\omega/2\pi \leq 100$ MHz, $\omega<<v\mu_a$ is obtained, so that $A(\omega)=[3(1-g)\mu_s\mu_a]^{\frac{1}{2}}$
$\sin B(\omega)=(\omega/2v\mu_a)$
$\cos B(\omega)=1$ thereby obtaining the following equations.

$$\Phi = (\sqrt{3}\ \omega r/2v) \times [(1-g)\mu_s/\mu_a]^{\frac{1}{2}} \quad (1.11)$$

$$I_p = [3SM(1-g)\mu_s/4\pi r]\exp\{-r[3(1-g)\mu_s\mu_a]^{\frac{1}{2}}\} \quad (1.12)$$

(2) $\omega \approx v\mu_a$

In this case, $f=\omega/2\pi \approx v\mu_a/2\pi=360$ MHz. Therefore, $A(\omega)=[3(1-g)\mu_s]^{\frac{1}{2}}(\omega/v)^{\frac{1}{2}}(2)^{\frac{1}{4}}$
$\sin B(\omega)=\sin(\pi/8)$ so that the following equation is obtained.

$$\Phi = 0.91 \times (\sqrt{3}\ \omega r/2v) \times [(1-g)\mu_s/\mu_a]^{\frac{1}{2}} \quad (1.13)$$

The amplitude $I_p$ can be similarly obtained, but a description of its calculation will be omitted below.

(3) $\omega \gg v\mu_a$

In this case, $f = \omega/2\pi \gg v\mu_a/2\pi = 360$ MHz. Therefore, $$A(\omega) = [3(1-g)\mu_s]^{\frac{1}{2}}(\omega/v)^{\frac{1}{2}}$$
$$\sin B(\omega) = \sin[(\frac{1}{2})\tan^{-1}(\omega/v\mu_a)]$$
$$= \sin\{(\frac{1}{2})[(\pi/2) - \cot^{-1}(\omega/v\mu_a)]\}$$
$$= \sin\{(\frac{1}{2})[(\pi/2) - \tan^{-1}(v\mu_a/\omega)]\}$$
$$= \sin[(\pi/4) - (v\mu_a/2\omega)]$$
$$= (1/\sqrt{2})[1 - (v\mu_a/2\omega)]$$
$$= (1/\sqrt{2})$$
$$\Phi = (3\omega/2v)^{\frac{1}{2}}r[(1-g)\mu_s]^{\frac{1}{2}} \quad (1.14)$$

If $\omega \gg v\mu_a$, then the phase difference $\Phi$ has a value not related to $\mu_a$, and any absorption information cannot be calculated. It should be noted that the $(1-g)\mu_s$ value can be obtained from (1.14) if $\omega \gg v\mu_a$.

(4) Examination of Errors

Errors produced upon approximation using equation (1.11) will be examined. When equation (1.11) is compared with equation (1.13), only coefficients are different from each other, and a ratio of the phase difference given by equation (1.13) to that by equation (1.11) is 0.91. If equation (1.11) obtained under the condition of $\omega \ll v\mu_a$ allows an error of 9% with respect to $\Phi$, this equation can be applied to a value near $\omega = v\mu_a$.

It is more important that equation (1.11) can be applied to $\omega$ for the range of $\omega \approx v\mu_a$ due to the elimination of the above coefficients in the calculation for obtaining the above ratio when a ratio of phase differences or a ratio of the squares of the phase differences is taken into consideration.

$$\Phi^2 = (3\omega^2 r^2/4v^2) \times [(1-g)\mu_s/\mu_a] \quad (1.15)$$

Judging from the above description, it is apparent that "the phase difference $\Phi$ to be measured in the present invention is in inverse proportion to the square root of the absorption coefficient $\mu_a$ within the range of a practically assumed angular frequency $\omega$ ($\omega \leq v\mu_a \approx 360$ MHz) or the absorption coefficient $\mu_a$ is in inverse proportion to the square $\Phi^2$ of the phase difference $\Phi$". The same operations as described above can also be performed for the amplitude $I_p$, and a description of its calculation will be omitted.

According to the present invention, as described above, the absorption information in the scattering medium is obtained using $\Phi$ or $\Phi^2$ having a simple and clear relationship with the absorption coefficient $\mu_a$. The values such as $\Phi$ and $\Phi^2$ are measured values, i.e., basic parameters which can be easily quantitatively measured from the detection signal. As will be described in detail, the influence of scattering can be easily eliminated by calculations such as divisions between these parameters obtained under different conditions.

(5) Measurement of Absorption Coefficient Ratio

The following conditions are assumed in measurements using light components having different wavelengths or measurements at different times or places.

If $\mu_a = \mu_{a1}$,
then $\Phi = \Phi_1$, $(1-g)\mu_s = (1-g)\mu_{s1}$, $r = r_1$ If $\mu_a = \mu_{a2}$,
then $\Phi = \Phi_2$, $(1-g)\mu_s = (1-g)\mu_{s2}$, $r = r_2$ Note that a change in g is incorporated in $\mu_{s1}$ and $\mu_{s2}$ because a change in $\mu_s$ is equivalent to a change in g.

Therefore, in the above assumptions, it may be assumed that $\mu_s$ or g is changed.

From equation (1.15)

$$\mu_{a1} = 3\omega^2 r_1^2 (1-g)\mu_{s1}/4v^2\Phi_1^2 \quad (1.16)$$

$$\mu_{a2} = 3\omega^2 r_2^2 (1-g)\mu_{s2}/4v^2\Phi_2^2 \quad (1.16)$$

so that $$\mu_{a2}/\mu_{a1} = (\Phi_1/\Phi_2)^2(\mu_{s2}/\mu_{s1})(r_2/r_1)^2 \quad (1.17)$$

$$\mu_{a2} - \mu_{a1} = (3\omega^2/4v^2) \times [\{(1-g)\mu_{s2}r_2^2/\Phi_2^2\} - \{(1-g)\mu_{s1}r_1^2/\Phi_1^2\}] \quad (1.18)$$

The following equation is generally established in the living body for near-infrared rays having a small wavelength difference:

$$(1-g)\mu_s = (1-g)\mu_{s1} = (1-g)\mu_{s2}$$

If $r_1 = r_2 = r$, equations (1.17) and (1.18) are rewritten as follows:

$$\mu_{a2}/\mu_{a1} = (\Phi_1/\Phi_2)^2 \quad (1.19)$$

$$\mu_{a2} - \mu_{a1} = (3\omega^2 r^2 (1-g)\mu_s/4v^2) \times [(1/\Phi_2^2) - (1/\Phi_1^2)] \quad (1.20)$$

A measurement method utilizing this relationship is equivalent to well-known dual-wavelength spectroscopy. Similar measurements can be performed in the present invention as follows.

It should be noted that the influence of the scattering constituent and the influence of the distance r are eliminated in equation (1.19). That is, the ratio of the squares of the phase differences is in inverse proportion to the absorption coefficient. This relationship is utilized to quantitatively measure the absorptive constituent and the degree of saturation of hemoglobins, and the like in the present invention. The $\mu_{a2}/\mu_{a1}$ and $(\mu_{a2} - \mu_{a1})$ values are average values of $\mu_{a2}/\mu_{a1}$ and $\mu_{a2} - \mu_{a1}$ along a straight line obtained by connecting the spot-like light incident point of the modulated light on the scattering medium and the photodetection point. If these values are regarded as linear integration values along the above straight line, simple imaging can be performed. Image reconstruction as in X-ray CT is performed to obtain a tomogram associated with $\mu_{a2}/\mu_{a1}$ and $\mu_{a2} - \mu_{a1}$. In addition, similar processing is performed to image distributions of the degree of saturation of hemoglobins and the absorptive constituents and to reconstruct a tomogram. As initially described, the approximated solution in a simple form derived from the photon diffusion equation is used. However, to improve the measurement precision, the strict phase difference may be used in place of the phase difference $\Phi$ as described above, as a matter of course.

(6) Differences between Present Invention and Report[11] Made by Sevick and Chance Differences in basic items between the present invention and the report[11] made by Sevick and Chance will be described below.

First of all, Sevick and Chance describe that $\Phi$ obtained above is almost equal to the average optical path length obtained by the time-resolved measurement method when the modulation frequency is low, i.e., $\omega << v\mu_a$. As described above, however, in the time-resolved measurement method, the average delay time (the barycenter of the output signal waveform) is obtained and multiplied with the speed of light in the scattering medium, thereby obtaining the average optical path length. In this case, the parameter directly obtained from the measurement data is the average delay time. The delay time changing with a change in an amount or concentration of absorptive constituent is very short. For example, if $\mu_a$ changes in 10%, an amount of change of the delay time with respect to the average delay time of 2.5 ns is about 5%, i.e., about 100 ps. It is difficult to measure this time difference in the conventional time-resolved measurement apparatus. In addition, the maximum incident light intensity with respect to the scattering medium such as a living body is limited, and a time-resolved waveform generally does not have a sufficiently high S/N ratio. It is difficult to obtain the above time difference. Their conclusion that it is impossible to obtain the absorption coefficient on the basis of the average optical path length calculated by a change in average delay time is reasonable.

An average delay time $t_{av}$ obtained by their time-resolved measurement method is derived from the Patterson's equation[6] representing the temporal waveform of the output light signal and is defined as follows.

$$t_{av} = (\sqrt{3}/2)(r/v)[(1-g)\mu_s/\mu_a]^{\frac{1}{2}}$$

Note that the symbols in the above equation are denoted by the same symbols as in the present invention.

The above equation is compared with equation (1.11) as follows.

$$\Phi = \omega t_{av} = 2\pi f t_{av}$$

The $\Phi$ value measured in the present invention is $2\pi f$ times the $t_{av}$ value obtained in the time-resolved measurement method.

The resolution considered using the ratio of the minimum measurable value to the full-scale value in the phase measurement is generally higher than that (nanosecond region) of the time-resolved measurement. Therefore, the present invention is superior to the time-resolved measurement.

Sevick and Chance analyze only the region in which the modulation frequency is very high, i.e., $\omega >> v\mu_a$ (the region of $\omega << v\mu_a$ is excluded due to the above reason). Their calculation formula is precisely analyzed in A1.4 (PP. 348-349) of reference[11]). Approximation may not be sufficient in the process of derivation of the formula, and the result is not correct accordingly. In the report of Sevick and Chance, measurement and imaging of the spatial distribution of the absorptive constituent in the scattering medium, and measurement of a tomogram are not described at all.

To the contrary, the present invention is applicable to a wide range from $\omega << v\mu_a$ to $\omega \approx v\mu_a$. In calculation of the absorption coefficient, a very simple relationship, i.e., an inverse proportion of the absorption coefficient $\mu_a$ to the square $\Phi^2$ of the phase difference, is utilized. In addition, the phase difference is a value easily obtained from the measurement value. The measurement precision is high, and the measurement errors are also small. A ratio of phase differences obtained at different conditions (to be described later) is calculated to eliminate the influence of the scattering constituent. It is possible to measure and image the spatial distribution of the absorptive constituent in the scattering medium and measure a tomogram.

3. Measurement of Absorption Information

As described above, the relationship between the absorption coefficient and the phase difference is obtained by equations (1.11) and (1.15). In measurements using light components having different wavelengths or measurements at different times or places, the relations given by equations (1.17) to (1.20) are utilized to perform various measurements. The principle of measurement for typical examples will be described below. The detailed arrangements of these measurement apparatuses will be described in detail in the description of preferred embodiments.

(1) Measurement of Degree of Saturation of Hemoglobins

Figure 4:
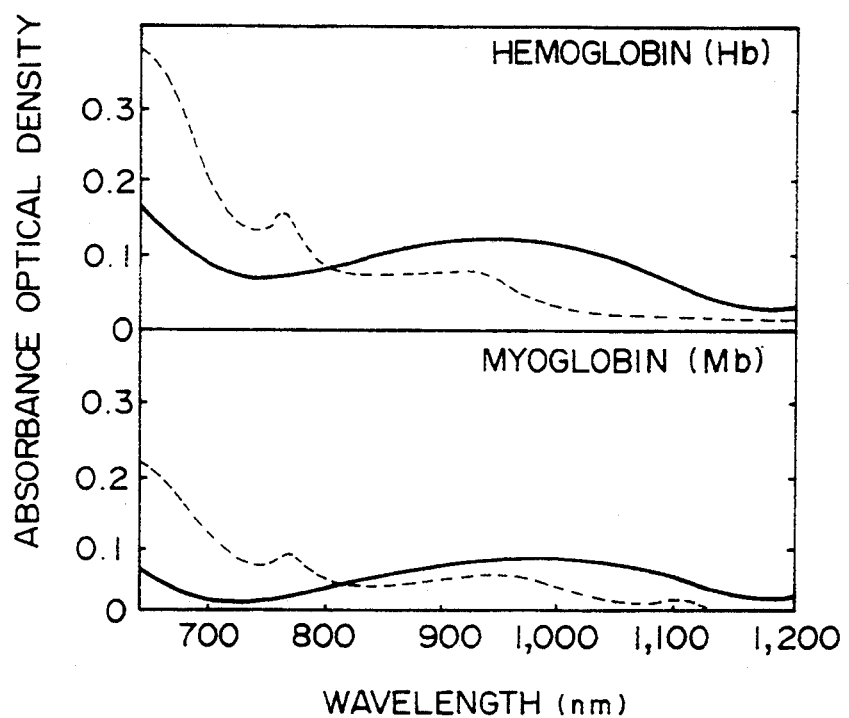
FIG. 4 is a graph showing absorption spectra of respective biological materials.

Main absorptive constituents in a mammalian brain are water, cytochrome, oxyhemoglobin, reduced hemoglobin. Absorption of water and cytochrome in a near-infrared range is as small as negligible with respect to an oxyhemoglobin and a reduced hemoglobin. The oxyhemoglobin and the reduced hemoglobin have different absorption spectra, as shown in FIG. 4. The skull is regarded as a scattering medium with respect to near-infrared rays.

Assume the basic frequency components of two modulated light components having wavelengths $\lambda_1$ and $\lambda_2$. Absorption coefficients at the wavelengths $\lambda_1$ and $\lambda_2$ can be obtained in accordance with the Lambert-Beer law as follows.

$\mu_{a1} = \epsilon_{Hb,1}[\text{Hb}] + \epsilon_{HbO,1}[\text{HbO}]$
$\mu_{a2} = \epsilon_{Hb,2}[\text{Hb}] + \epsilon_{HbO,2}[\text{HbO}]$ where $\epsilon_{Hb,1}$: the molar absorption coefficient [mm$^{-1}$·M$^{-1}$] of the reduced hemoglobin at the wavelength $\lambda_1$
$\epsilon_{HbO,1}$: the molar absorption coefficient [mm$^{-1}$·M$^{-1}$] of the oxyhemoglobin at the wavelength $\lambda_1$
$\epsilon_{Hb,2}$: the molar absorption coefficient [mm$^{-1}$·M$^{-1}$] of the reduced hemoglobin at the wavelength $\lambda_2$
$\epsilon_{HbO,2}$: the molar absorption coefficient [mm$^{-1}$·M$^{-1}$] of the oxyhemoglobin at the wavelength $\lambda_2$
[Hb]: the molar concentration [M] of the reduced hemoglobin
[HbO]: the molar concentration [M] of the oxyhemoglobin Since the degree Y of saturation is given as follows:
$Y = [\text{HbO}]/([\text{Hb}] + [\text{HbO}])$
the following equation is obtained.

$$\mu_{a1}/\mu_{a2} = [\epsilon_{Hb,1} + Y(\epsilon_{HbO,1} - \epsilon_{Hb,1})] \div [\epsilon_{Hb,2} + Y(\epsilon_{HbO,2} - \epsilon_{Hb,2})]$$

Measurements under the same setup condition make it possible to obtain the same distance r, so that the following equation can be derived from equation (1.19):

$$\mu_{a1}/\mu_{a2} = (\Phi_2/\Phi_1)^2$$

Therefore, Y is calculated from the known parameters $\epsilon_{Hb,1}$, $\epsilon_{HbO,1}$, $\epsilon_{Hb,2}$, and $\epsilon_{HbO,2}$ and the measurement values $\Phi_2$ and $\Phi_1$.

If $\mu_{s1} \neq \mu_{s2}$, then this ratio is given by another measurement or estimation to obtain Y. In this case, a measurement may be performed with modulated light having $\omega$ satisfying $\omega >> \mu_a$ to obtain $(1-g)\mu_s$ from equation (1.14).

If a waveform ($\approx 800$ nm, isosbestic wavelength) for obtaining the same absorption level for both an oxyhemoglobin and a reduced hemoglobin is used, the above equation can be made simpler.

(2) Presence of Background Absorption

Background absorption may not be neglected in a living body. In this case, if the background absorption levels at the wavelengths $\lambda_1$, $\lambda_2$, and $\lambda_3$ are defined as $a_1$, $a_2$, and $a_3$, the following equations are established in accordance with the Lambert-Beer law.

$$\mu_{a1} = \epsilon_{Hb,1}[Hb] + \epsilon_{HbO,1}[HbO] + a_1$$

$$\mu_{a2} = \epsilon_{Hb,2}[Hb] + \epsilon_{HbO,2}[HbO] + a_2$$

$$\mu_{a3} = \epsilon_{Hb,3}[Hb] + \epsilon_{HbO,3}[HbO] + a_3$$

The above equations are rearranged to obtain the following equation:

$$(\mu_{a1} - \mu_{a2})/(\mu_{a3} - \mu_{a2}) = [(\epsilon_{Hb,1} - \epsilon_{Hb,2}) + Y(\epsilon_{HbO,1} - \epsilon_{HbO,2} - \epsilon_{Hb,1} + \epsilon_{Hb,2}) + K(a_3 - a_2)] \div [(\epsilon_{Hb,3} - \epsilon_{Hb,2}) + Y(\epsilon_{HbO,3} - \epsilon_{HbO,2} - \epsilon_{Hb,3} + \epsilon_{Hb,2}) + K(a_3 - a_2)]$$

for $K = 1/([Hb] + [HbO])$

If $(a_1 - a_2) \approx (a_3 - a_2) \approx 0$, the degree Y of saturation can be obtained in the same manner as described above.

The above condition $(a_1 - a_2) \approx (a_3 - a_2) \approx 0$ can be achieved by properly selecting a wavelength for a living body.

(3) Measurement of Change in the Concentration Absorptive Constituents over Time The measurements shown in (1) and (2) are performed at different times, and differences between the resultant values are obtained to measure changes in the concentration of absorptive constituent over time. If an appropriate wavelength is selected so that the presence of a single absorptive constituent in the scattering body is determined, the above equation can be apparently made simpler.

(4) Imaging

As described above, the measurement values of the absorption information obtained in (1) to (3) are regarded as the linear integration values of the absorption information in the scattering medium along the straight line obtained by connecting the spot-like modulated light incident position to the photodetection point. If the above measurements are performed at a lots of locations in a relatively thin (the distance r is short) scattering medium, the measurement of a two-dimensional distribution, i.e., imaging can be performed. In this case, a plurality of photodetectors can be used.

In this case, it is more convenient to use values normalized with the distance r. The distance r can be easily measured using a general distance measurement apparatus.

The simplest imaging is imaging of the distribution of absorption coefficients in the scattering medium. With reference to a phase difference at a given measurement position, the square of a ratio of this phase difference to that at another position is obtained to obtain image data at each position. If the distance r changes, the absorption coefficients normalized with the distance r can be used in the same manner as described above.

(5) Measurement of Tomogram

Measurements of the above linear integration value for various angle along the slice of the scattering medium are performed to obtain data as in (1) to (3), and a tomogram can be obtained as in X-ray CT. In this case, values normalized with the distance r are used.

As described in (4), the ratio of the absorption coefficient at the given reference position to that at another position may be obtained to reconstruct a tomogram of the distribution of absorption coefficients. In this case, absorption coefficient values normalized with the distance r are used.

(6) Arrangement of Measurement Apparatus

Figure 5:
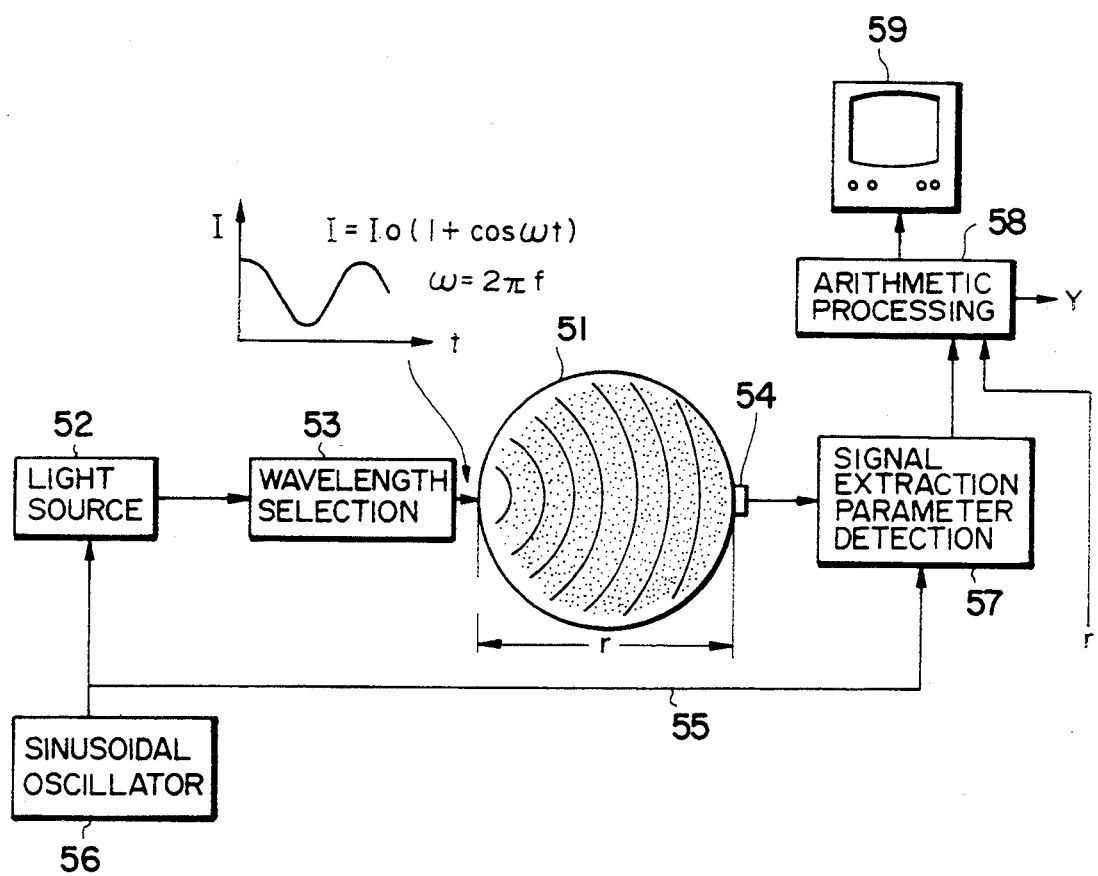
FIG. 5 is a diagram showing an apparatus for measuring absorption information in a scattering medium.

FIG. 5 shows a detailed arrangement of an apparatus for measuring absorption information in a scattering medium 51 according to the present invention. A light source 22 emits modulated light components having two desired wavelengths. One of the modulated light components from the light source is selected by wavelength selector 63, and the modulated light having the desired wavelength is incident on one point on the surface of the scattering medium as the object to be measured. Light propagating through the scattering medium is detected by a photodetector 54. The photodetector is located on the side opposite to the light source with respect to the scattering medium. It has a small aperture. A first unit 57 extracts one of the frequency components comprising the modulated light, e.g., the sinusoidal wave of a fundamental frequency component, from a signal from the photodetector. The extracted frequency component is compared with a 55 (e.g. sinusoidal wave generated by sinusoidal oscillator) synchronized with the light source, thereby obtaining a parameter, e.g., a phase difference, associated with the propagating wave. A second unit 58 calculates first absorption information and second absorption information on the basis of this parameter. More specifically, since the phase difference as the parameter is in inverse proportion to the square root of the absorption coefficient in the scattering medium, this relation is utilized to calculate a signal A proportional to the absorption coefficient. A signal B proportional to an absorption coefficient with respect to the modulated light having the other wavelength is obtained in the same manner as described above. The signals A and B constitute the first absorption information. The second absorption information in the scattering medium, e.g., a signal representing the degree of saturation of hemoglobins, is arithmetically obtained from the signals A and B and the known optical parameters for these two wavelengths.

The incident position of the modulated light incident on the scattering medium and the position of the photodetection point are scanned (not shown) to obtain the degree of saturation of hemoglobins at each portion in the scattering medium, and the resultant values are stored in a frame memory (not shown). The stored data is read out from the frame memory in accordance with a television scheme 59, thereby obtaining an image representing the distribution of the degree of saturation. In this case, the distance r between the incident position of the modulated light and the photodetection point is measured, and a normalized value (the above signal proportional to the absorption is normalized by the distance r) is used.

If background absorption is present, the same measurements as described above are performed for modulated light components having three different wavelengths. Imaging of the distribution of the normalized absorption coefficients and reconstruction of a tomogram can also be performed.

The arrangements of the respective components of the absorption information measurement apparatus will be described below in detail.

Figure 6A:
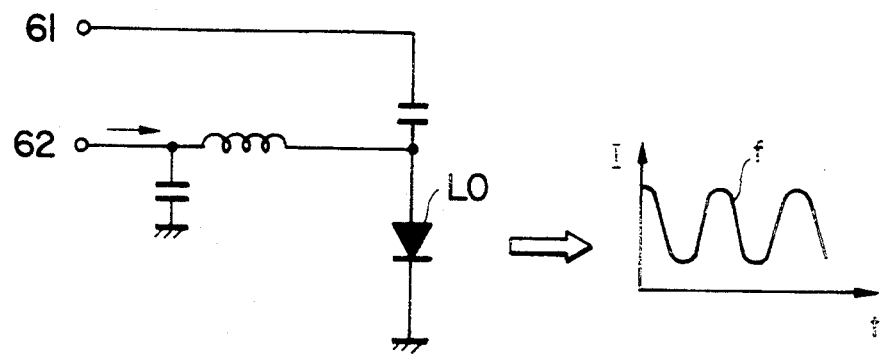
FIGS. 6A to 6C are views showing an example of generation of modulated light.
Figure 6B:
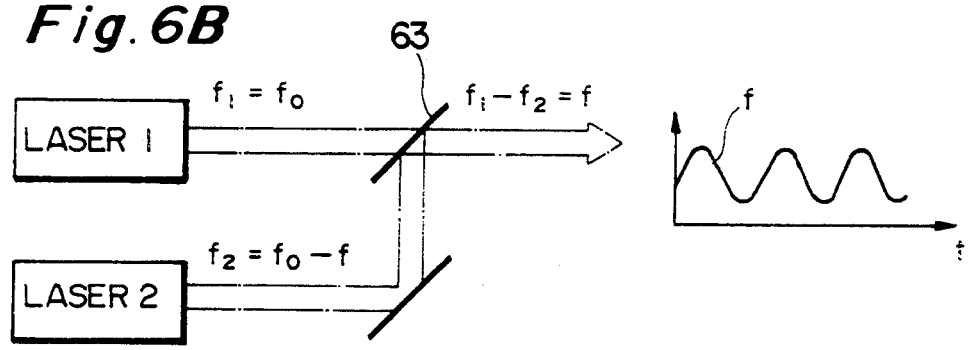
Figure 6C:
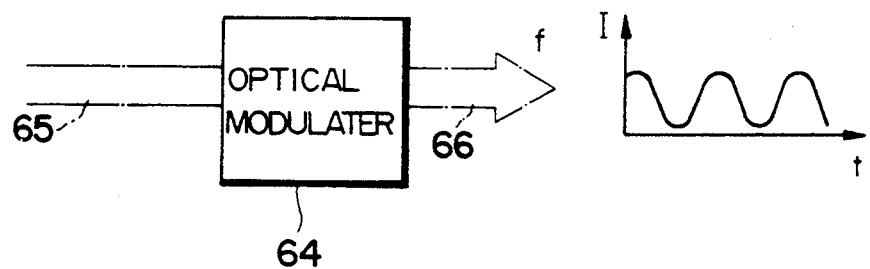
Figure 7A:
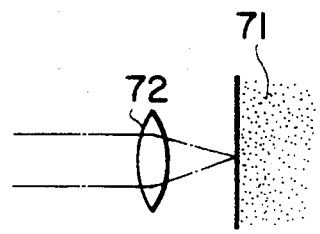
FIGS. 7A to 7D are views showing an example of incidence of modulated light on a scattering medium.
Figure 7B:
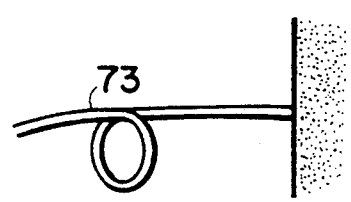
Figure 7C:
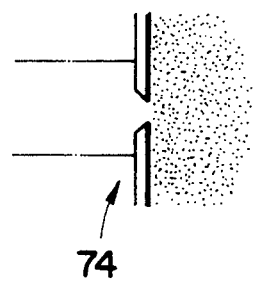
Figure 7D:
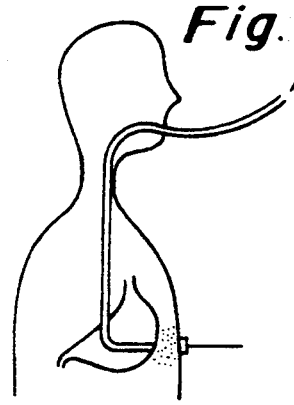

As shown in FIGS. 6A–6C, modulated light is generated utilizing current modulation of a laser diode LD based on a sinusoidal wave 61 and a DC power source output 62 (FIG. 6A), a beat of two CW laser beams via half mirrors 63 (FIG. 6B), or an optical modulator 64 converting a laser beam 65 to modulated light 66 (FIG. 6C). To cause this modulated light to be incident on a scattering medium 71, a method utilizing a condenser lens 72 (FIG. 7A), an optical fiber 73 (FIG. 7B), a pinhole 74 (FIG. 7C), or a modulated light incident method using a gastrocamera (FIG. 7D) or the like may be used.

Figure 8A:
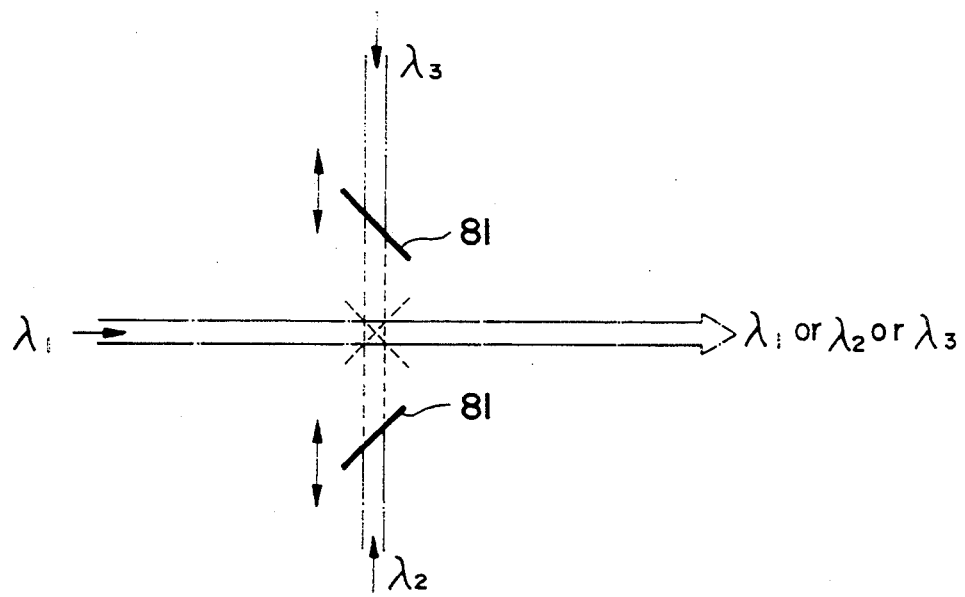
FIGS. 8A and 8B are views showing an example for selecting one of modulated light components having different wavelengths.
Figure 8B:
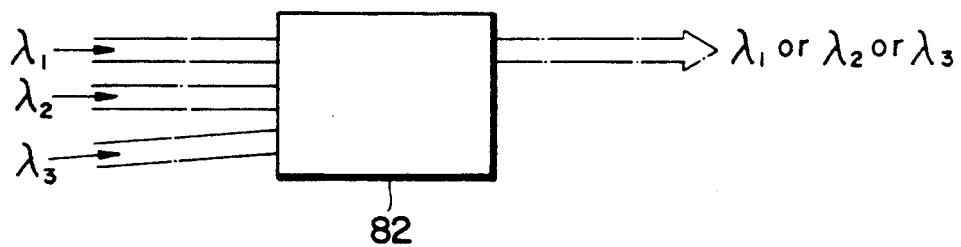

One of the modulated light components having desired wavelengths is selected by mirror 81 switching (FIG. 8A), switching using an optical switch 82 (FIG. 8B), or the like. The modulated light components having desired wavelengths may be coaxially formed and may be selected by a wavelength selection filter (spectral band pass filter) at a position just before the light incident position or at a position before a photodetector upon direct incidence of these parallel modulated light components on the scattering medium.

Figure 9A:
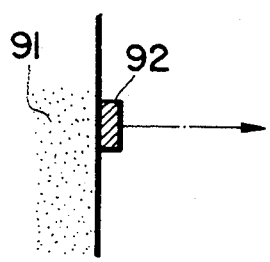
FIGS. 9A to 9D are views showing an example of modulated light detection.
Figure 9B:
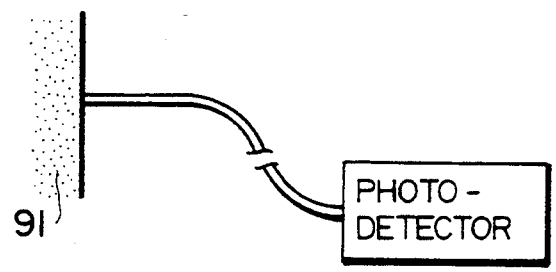
Figure 9C:
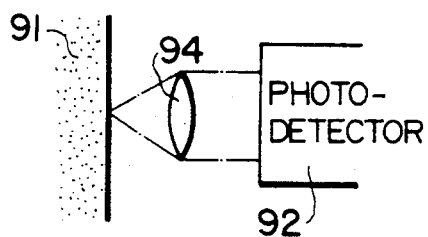
Figure 9D:
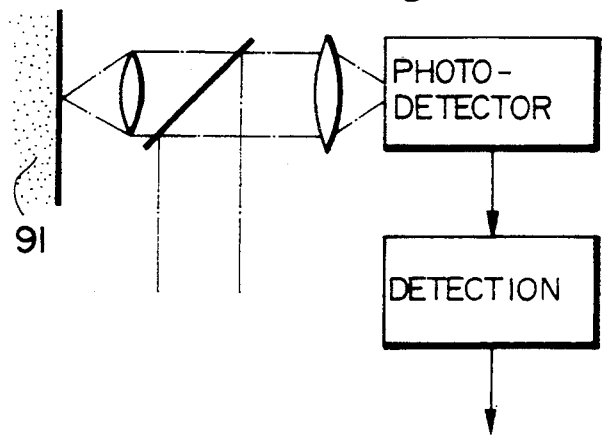

A means for detecting the modulated light propagating through the scattering medium 91 may be constituted by direct photodetection 92 (FIG. 9A), a method of detecting the light through an optical fiber 93, a lens 94 (FIGS. 9B and 9C), a heterodyne detection method of a specific frequency component (FIG. 9D), or the like.

Figure 10A:
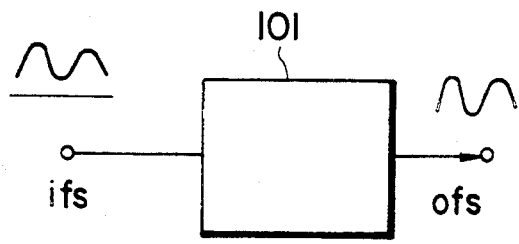
FIGS. 10A to 10C are diagrams showing examples of extracting a specific frequency component signal.
Figure 10B:
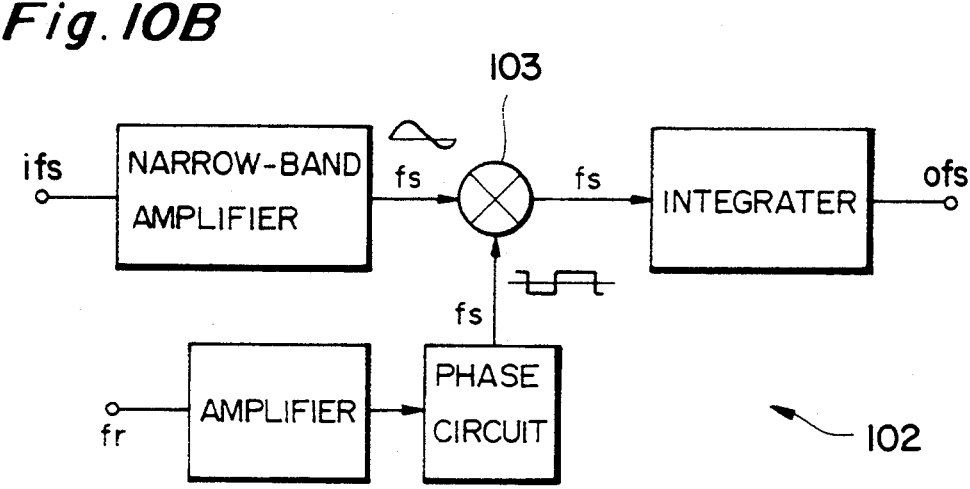
Figure 10C:
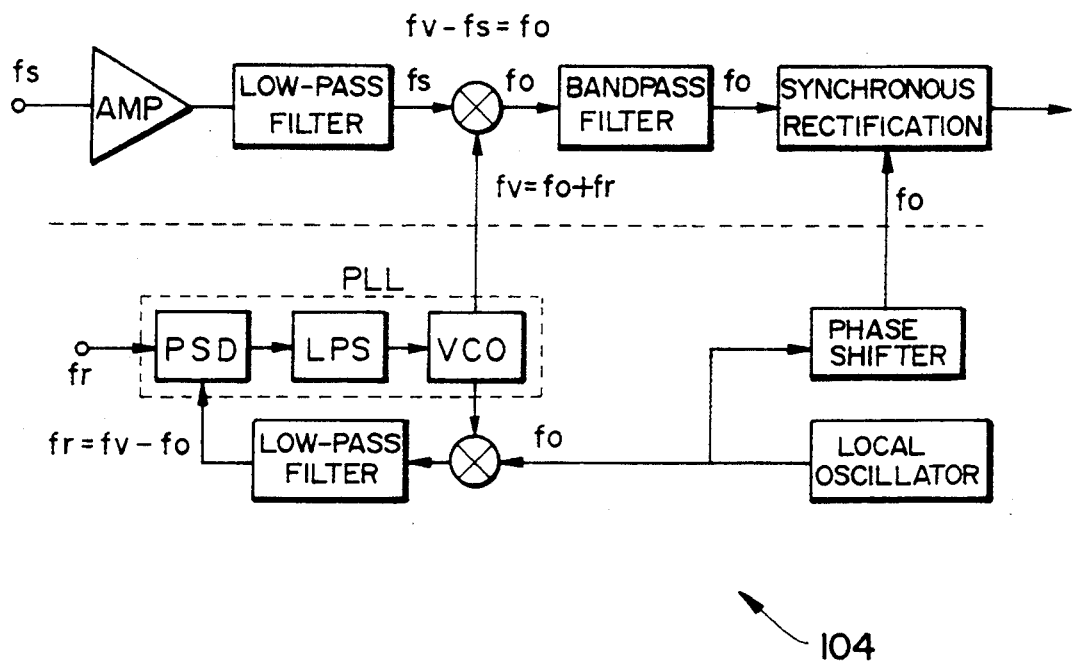

The means for detecting an input signal if having the specific frequency signal to generate an output frequency signal ofs may be constituted by a method using a narrow-band amplifier 101 (FIG. 10A), a method using a lock-in amplifier 102 based on a reference signal rs and a synchronous rectifying circuit 103 (FIG. 10B), a heterodyne type lock-in amplifier 104 (FIG. 10C), or the like. The heterodyne type lock-in amplifier having a phase-locked loop PLL comprised of a voltage controlled oscillator VCO, a phase sensitive detector PSD and a low-pass filter LPS.

Figure 11A:
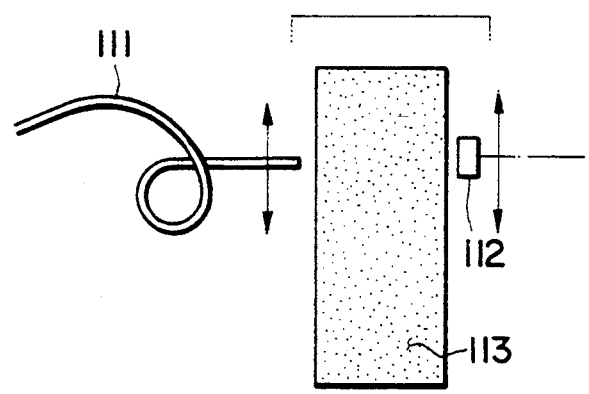
FIGS. 11A and 11B are views showing an example of scanning for imaging.
Figure 11B:
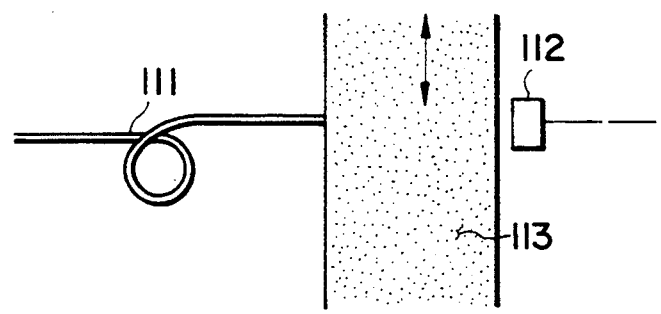
Figure 12:
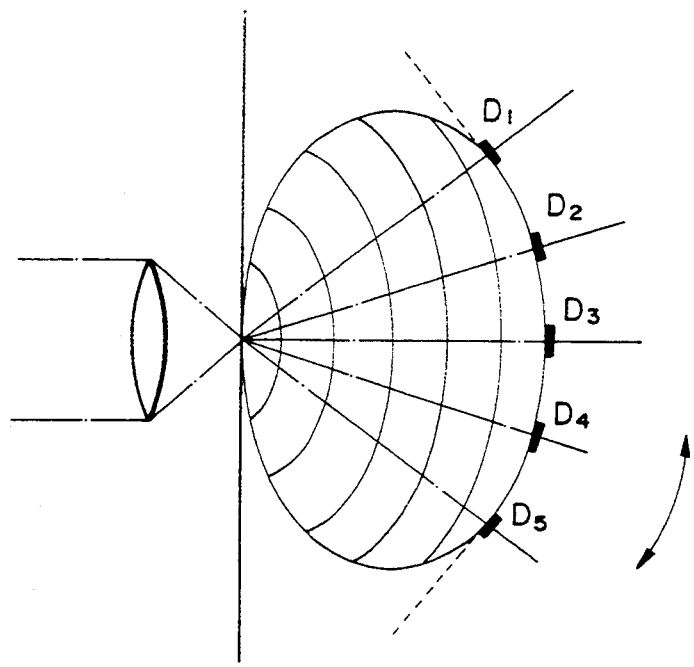
FIG. 12 is a view showing a method utilizing a plurality of photodetection paths.

A scanning means for imaging may be constituted by a method of synchronously scanning the pair of light source (i.e. optical fiber 111) and photodetector 112 (FIG. 11A), a method of moving the scattering medium 113 as the object to be measured (FIG. 11B), or the like. To measure a tomogram, rotary scanning of the scattering medium or the pair of light source and photodetector is required as in X-ray CT. Rotary scanning may be performed simultaneously with translational scanning. In addition, as shown in FIG. 12, a method of causing a plurality of photodetectors $D_1$, $D_2$, ... to detect a wave concentrically spherically propagating through the scattering medium is also available, the detection being rotatably performed in an auxiliary scanning direction.

The selection, detection, scanning, and the like of the modulated light, as described above, can be applied to a case in which a light source generates a repetition pulse.

Arithmetic processing of the degree of saturation of hemoglobins in a scattering medium, other absorption information, and a tomogram thereof is performed at high speed using a computer having a memory and a display.

4. Detailed Embodiments (1) First Embodiment

The first embodiment exemplifying the apparatus for measuring absorption information in a scattering medium according to the present invention is shown in FIG. 13.

A light source 2 using a laser diode (LD) or the like generates modulated light $I = I_0(1 + M\cos\omega t)$ where M is the degree of modulation, $\omega$ is angular frequency ($\omega = 2\pi f$), and t is time. The wavelength of light from the light source must be appropriately selected in accordance with an object to be measured. Light having a wavelength of 600 nm or more generally tends to be transmitted through a living body in association with absorption of a hemoglobin or the like. The oxyhemoglobin and the reduced hemoglobin have different spectral transmittances, as shown in FIG. 4. If an appropriate wavelength is selected to distinguish the oxyhemoglobin from the reduced hemoglobin. If an isosbestic wavelength where absorption coefficient is same for both the oxyhemoglobin and the reduced hemoglobin is used, the sum of the oxyhemoglobins and the reduced hemoglobins can be measured. If the frequency f in the modulation frequency $f = \omega/2\pi$ is higher, the spatial resolution of imaging or the like can be improved, but attenuation becomes undesirably large. Various light sources such as an He-Ne laser can be used in addition to the LD. However, since modulated light must be generated, a light source 2 which requires a simple modulation mechanism and a simple circuit is advantageously selected. The light source may be a pulse light source.

The degree of modulation is preferably large, but may be small. The magnitude of the degree of modulation is not an essential problem in the present invention. The degree of modulation is determined in favor of the arrangement of the modulation apparatus. When an LD is used as the light source, modulated light of 1 MHz to 1 GHz can be easily generated. This is a method used in the field of optical communications. A pumping current of the LD is modulated with a sinusoidal wave of 1 MHz to 1 GHz. When the frequency exceeds 1 GHz, an LD having good frequency characteristics and a high-frequency circuit are required. In an He-Ne laser, the resonator length of one laser is differentiated from that of the other laser to synthesize two laser beams, thereby easily obtaining a beat signal having a frequency difference. This beat signal can be advantageously used.

The modulated light from the light source described above is incident on an object 22 to be measured through an optical fiber 4. In this case, collimated light may be focused by a lens and incident on the scattering medium 22, or the collimated light may be incident on the scattering medium through an aperture. That is, a diffusion length $l_d$ in the scattering medium is, e.g., 1 to 3 mm in a living body. The incident light is almost perfectly scattered until it propagates by $l_d$ in the direction of optical axis. From a position spaced apart from the light incident position by $l_d$ in the scattering medium, the influence of directivity of the incident light is almost zero. Therefore, the incident light must satisfy only the condition that it is incident as a small light spot on a scattering medium having a thickness of several mm or more.

FIG. 13 also shows distance measuring unit 20 whose output is operated on by arithmetic processing units I and II (15,16) to produce a signal to be displayed on display/recording apparatus 18.

Figure 14A:
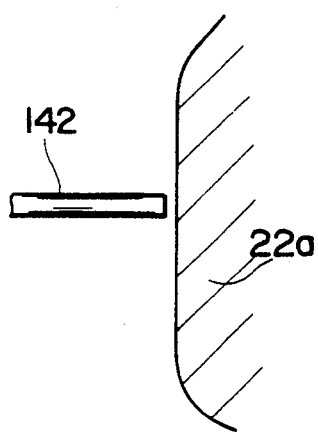
FIGS. 14A and 14B are views showing modulated light incident methods.
Figure 14B:
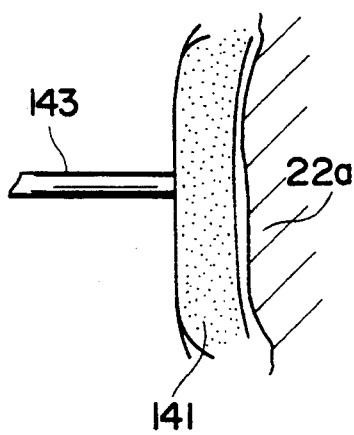

A space between the optical fiber 4 and the object 22 is very small in the drawing of the embodiment in FIG. 13. However, in practice, this space may be increased, and a liquid material or jelly-like material (to be referred to an interface material hereinafter) having almost the same refractive index and scattering coefficient as those of the object 22 may be filled in this space. FIGS. 14A and 14B show comparison of the presence/absence of the interface material. More specifically, FIG. 14A shows a case in which an optical fiber 142 directly contacts the object 22a, and FIG. 14B shows a case in which an optical fiber 143 contacts the object 22a through an interface material 141. In FIG. 14B, since the modulated frequency component represented by equation (1.5) coherently propagates in the interface material filled in the space and is incident on the object 22, no practical problem is posed.

A photodetector 8 has an aperture 6 for controlling an effective area of light-receiving. The aperture 6 may be a hole formed in an opaque plate. When light is guided to the photodetector through an optical fiber or a light guide, the end face of the optical fiber or the like serves as an effective aperture. In either case, it is preferable to have a structure in which light incident on a portion except the active area of the photodetector is shielded. In addition, the interface medium may be inserted between the photodetection aperture 6 and the object 22.

Any photodetector such as a phototube, a photodiode, an avalanche photodiode, or a PIN diode can be used as the photodetector 8 in place of a photon multiplier tube. Any photodetector can be selected if it has frequency characteristics enough to detect the modulated frequency component and spectral sensitivity characteristics sufficient for the incident light. If output light is weakened, a high-sensitivity photodetector is used.

Figure 15:
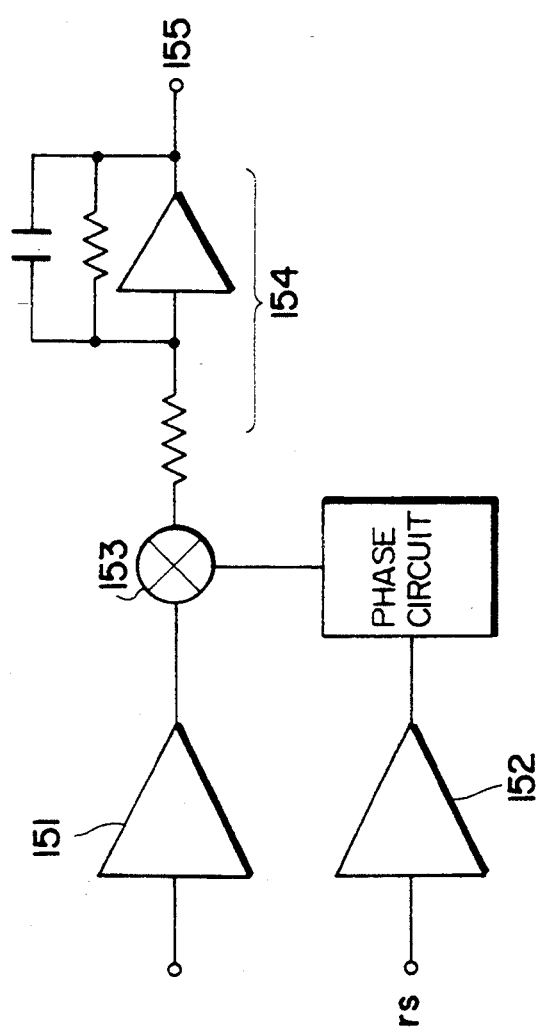
FIG. 15 is a diagram showing the arrangement of the main part of a lock-in amplifier.

An output signal from the photodetector is input to a lock-in amplifier 10 which includes signal extraction unit 11 and parameter detection unit 12. The lock-in amplifier 10 extracts a modulated frequency component signal from the photodetection signal to measure a phase difference and an amplitude. FIG. 15 shows the main part of this lock-in amplifier.

The lock-in amplifier is a device capable of precisely selecting and detecting only a component having the same frequency as a reference signal from a repeated weak signal mixed in noise. The weak input signal is amplified with a narrow band amplifier 151, and the amplified signal is synchronously rectified (also called phase sensitive detection) by a multiplier 153, and an integration value thereof is output. Any reference signal RS can be used if it is synchronized with the input signal, the reference signal being amplified by amplifier 152. In this embodiment, a modulation signal used for generating modulated light or a signal obtained upon reception of the modulated light is used. The output of multiplier 153 is operated on by integrator 154 to generate output 155.

Figures 16A, 16B, 16C, 16D, 16E:
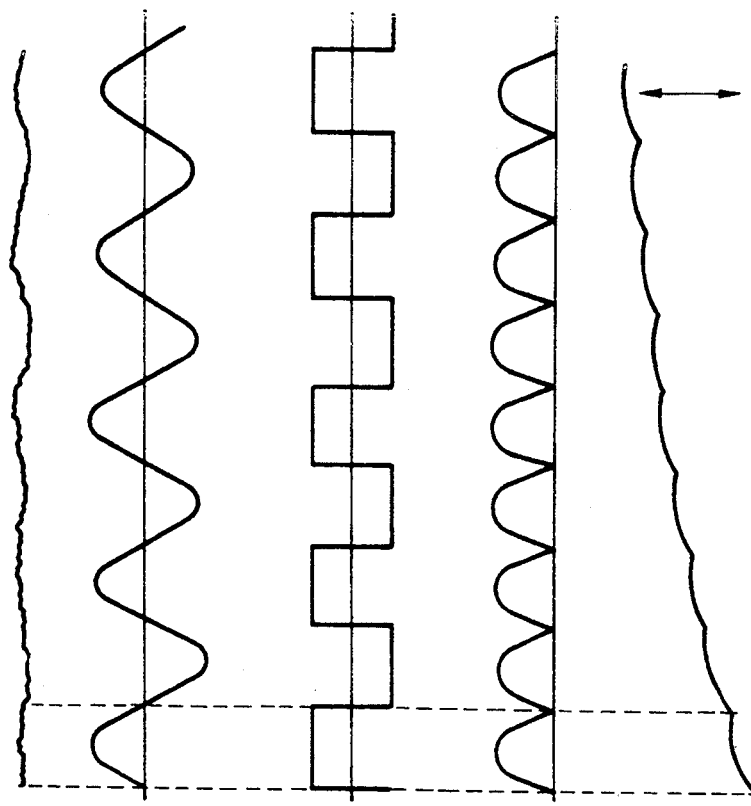
FIGS. 16(a)-16(e) show relationships between waveforms of the respective components in the lock-in amplifier.
Figures 17A, 17B, 17C:
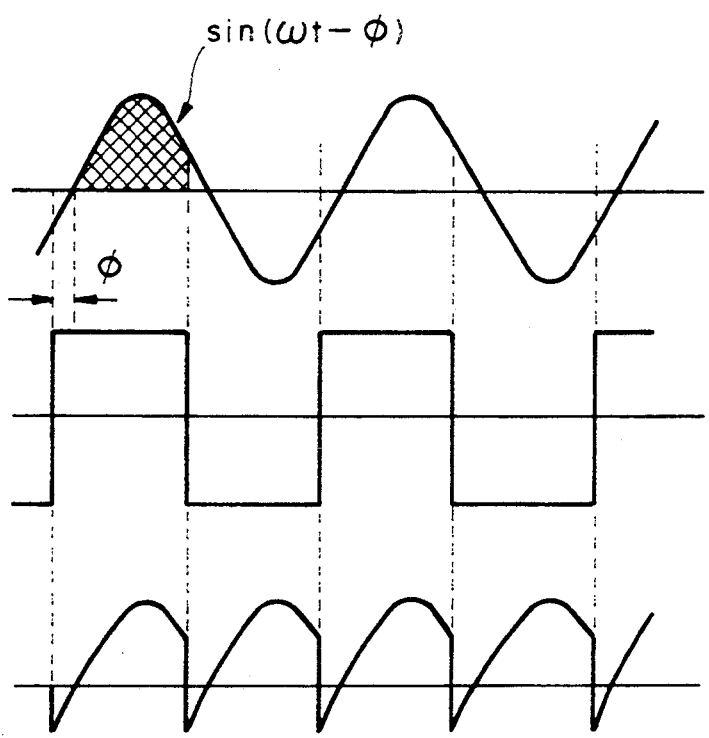
FIGS. 17(a)-17(c) show relationships between a phase shift.

The waveforms of the respective signals in this lock-in amplifier are shown in FIGS. 16(a)–16(e). FIG. 16 shows an input signal, FIG. 16(b) shows an output from the narrow-band amplifier, FIG. 16(c) shows an output from a phase circuit, FIG. 16(d) shows an output from the multiplier, and FIG. 16(e) shows an output from the integrator. The S/N ratio of the detection system using the lock-in amplifier is determined by an equivalent noise bandwidth $\Delta f$ of the system and is in inverse proportion to $(\Delta f)^{\frac{1}{2}}$. In this lock-in amplifier, as shown in FIGS. 17(a)–17(c), an output corresponding to a signal $\sin(\omega t - \Phi)$ (FIG. 17(a)), which is phase-delayed by $\Phi$ from the reference signal (FIG. 17(b)), is $A\cos\Phi$ (FIG. 17(c)), where A is a constant.

A commercially available lock-in amplifier responds to several MHz. In a lock-in amplifier of several MHz to 1 GHz, the operational principle is the same as that of the above commercially available lock-in amplifier, but must be arranged using a high-speed electronic device. In the region of several MHz to 1 GHz, a heterodyne amplifier is generally connected to the input to the narrow-band amplifier in FIG. 15. This lock-in amplifier is called a heterodyne type lock-in amplifier. The arrangement of this heterodyne type lock-in amplifier has been described in FIG. 10C. The heterodyne amplifier converts the input signal into a signal representing a difference in frequency between the input signal and a local oscillator. This difference signal, i.e., a signal having an intermediate frequency of several MHz or less is input to the lock-in amplifier described above. In this case, the reference signal rs is a signal synchronized with the intermediate frequency.

A conventional lock-in amplifier 10 outputs two orthogonal amplitude components ($\sin\Phi$ and $\cos\Phi$) and a phase difference $\Phi$. The function of generating these outputs is represented as a parameter detector 12 in the lock-in amplifier 10 in FIG. 13. In this embodiment, the phase difference $\Phi$ is used.

This phase difference $\Phi$ corresponds to the phase difference $\Phi$ in equations (1.6), (1.11) and (1.15) described above. As indicated by these equations, the phase difference $\Phi$ is approximately in inverse proportion to the square root of the absorption coefficient $\mu_a$ in the scattering medium 22 and is in proportion to the distance r. In this case, since the distance r is given as a constant, an arithmetic processing circuit 15 calculates a square $\Phi^2$ of the phase difference serving as the fist absorption information by using r as the constant (arithmetic processing I). The calculated value $\Phi^2$ is input to a next arithmetic processing circuit 16.

A second measurement identical to the first measurement described above is performed at another time, i.e., $t_1$ seconds after the first measurement in the same arrangement to calculate a phase difference $\Phi_1$ and then $\Phi_1^2$. The resultant value $\Phi_1^2$ is output to the arithmetic processing circuit 16.

The arithmetic processing circuit 16 calculates a ratio $\Phi^2/\Phi_1^2$ serving as the second absorption information using $\Phi^2$ as the reference value (arithmetic processing II). If the influences of the scattering constituents at two different times, i.e., $(1-g)\mu_s$ values are identical, the ratio $\Phi^2/\Phi_1^2 = \mu_{a1}/\mu_a$ from equation (1.15) because the distance r is constant. That is, a change in absorption coefficient is obtained. When the above measurement is continuously performed to measure changes in absorption coefficients as a ratio to the reference value. The arithmetic processing circuit 16 has a function of storing these values, and these values are displayed and/or recorded by display unit 18. If the $(1-g)\mu_s$ values are different from each other, the ratio $\Phi^2/\Phi_1^2$ is obtained using these measurement values or an estimation value.

In the embodiment shown in FIG. 13, a pair of photodetection point and incident point of the modulated light incident on the scattering medium serving as the object 22 may be scanned or moved (not shown). In this case, the above measurements are identical to measurements performed at different locations and different times. Assuming that the measurement distance r is constant at different measurement positions and the object to be measured is set in a steady state, $\Phi^2/\Phi_1^2$ becomes equal to $\mu_{a1}/\mu_a$ from equation (1.19). That is, the ratio of the absorption coefficient $\mu_{a1}$ at another position to the absorption coefficient $\mu_a$ at the reference position can be measured. Therefore, the above measurements are performed at a lots of positions to measure the distribution of absorption coefficients.

In the above description, the distance r is set constant. However, if the distance changes depending on different positions, a distance measurement unit 20 for measuring the distance r in synchronism with the photodetector 8 may be used. An output signal from the distance measurement unit 20 is input to the arithmetic processing circuit 15 to obtain a quotient of the phase difference and the distance r, thereby normalizing the phase difference. Therefore, even if the distance r changes depending on positions, the distribution of absorption coefficients can be measured.

(2) Second Embodiment

Figure 18:
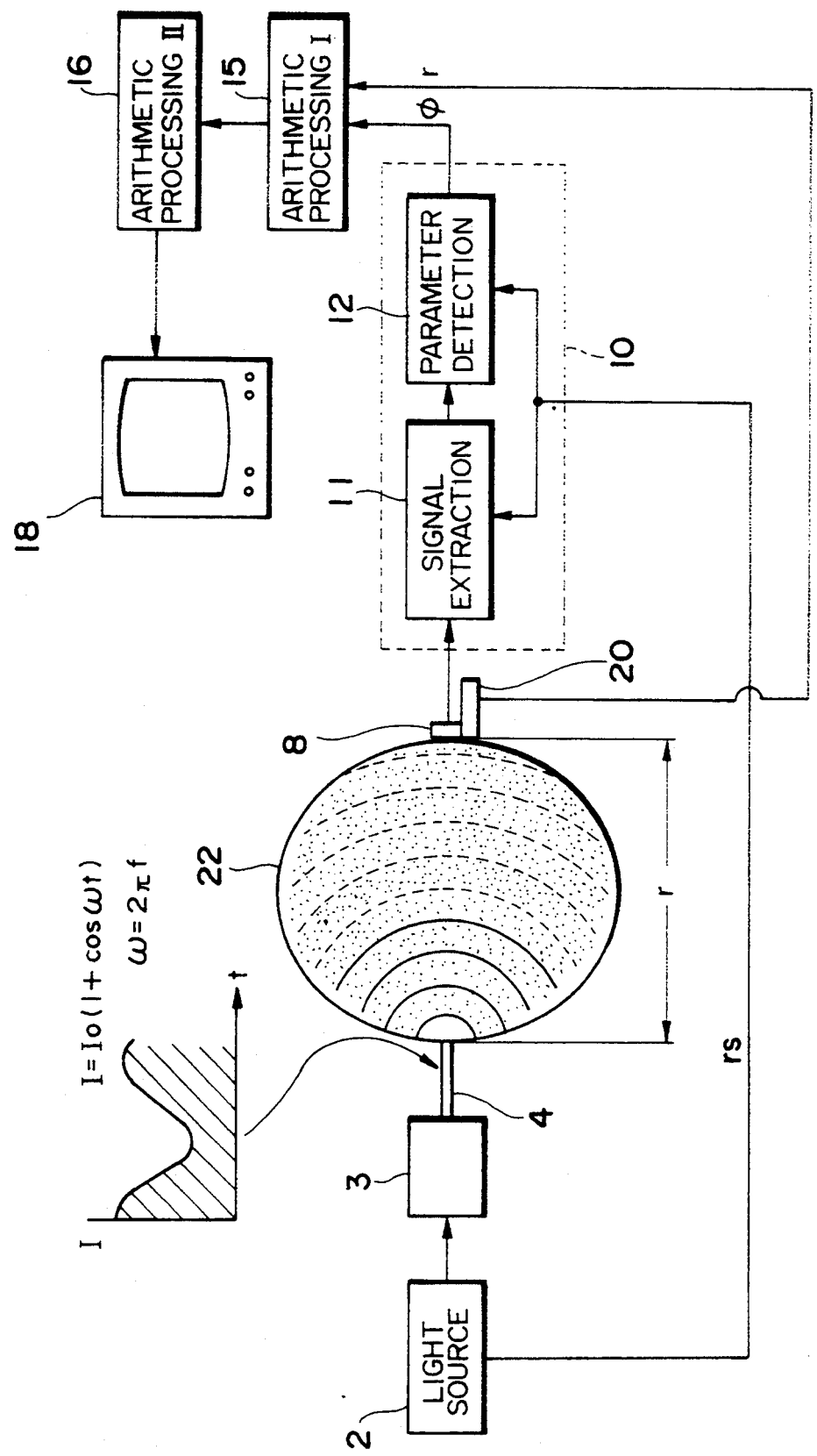
FIG. 18 is a diagram showing an arrangement of the second embodiment.

FIG. 18 shows an apparatus for measuring absorption information in a scattering medium according to the second embodiment. This apparatus measures the degree of saturation of hemoglobins. In the first embodiment, the modulated light having one wavelength is used. In the second embodiment, however, modulated light components having two or more different wavelengths are used. Other arrangements in the second embodiment are the same as those in the first embodiment.

A light source 2 generates modulated light components $I=I_0(1+M\cos\omega t)$ having two or more different wavelengths. The same reference numerals as in the first embodiment denote the same parts in the second embodiment. These modulated light components having different wavelengths may be generated by individual modulated light generators, respectively. The method described with reference to the first embodiment applies to this.

One of the modulated light components having different wavelengths is selected by a wavelength selector 3. In this case, a mirror is used to select a desired modulated light component. However, an optical switch may be used to select the desired one, as described above.

The selected modulated light component is incident on a scattering medium serving as an object 22 to be measured through an optical fiber 4. In this case, as in the first embodiment, interface materials may be inserted between the object 22 and an optical fiber 4 and between the object 22 and an apertured photodetector 8.

In this embodiment, the apertured photodetector is used. The various arrangements described above can be used for this photodetector and the aperture.

An output from the photodetector is input to a lock-in amplifier 10 as in the first embodiment. A modulated frequency component signal is extracted by the lock-in amplifier 10 to detect a phase difference $\Phi_1$. A suffix represents a wavelength $\lambda_1$ of the modulated light.

This phase difference $\Phi_1$ is in inverse proportion to the square of the absorption coefficient $\mu_{a1}$ of the absorptive constituent of the scattering medium and is proportional to a distance r, as indicated by equation (1.11). An arithmetic processing circuit 15 calculates $\Phi_1^2/r$ serving as the first absorption information using $\Phi_1$ (arithmetic processing I). Note that $(1-g)$ is dealt as a constant. Another modulated light components having different wavelengths is selected by the wavelength selector 3. The same measurement as described above is performed. The arithmetic processing circuit 15 calculates $\Phi_2^2/r$ at another wavelength $\mu_2$. The same measurement gives $\Phi_3^2/r$ at a wavelength $\lambda_3$.

An arithmetic processing circuit 16 calculates a degree of saturation of hemoglobins which serves as second absorption information from the above arithmetic result and the known parameters in accordance with the method described above (arithmetic processing II).

If the measurement point is fixed, the distance r can be regarded as a constant in the arithmetic operation in the arithmetic processing circuit 15.

When the above measurement is continuously and repeatedly performed over time, a change in the degree of saturation of hemoglobins over time can be calculated.

When an appropriate means (not shown) for scanning the positional relationship between the object to be measured and the pair of photodetection point and incident point of the modulated light component is utilized to perform a measurement, i.e., imaging, of the spatial distribution of the degree of hemoglobins as in the first embodiment.

(3) Third Embodiment

Figure 19:
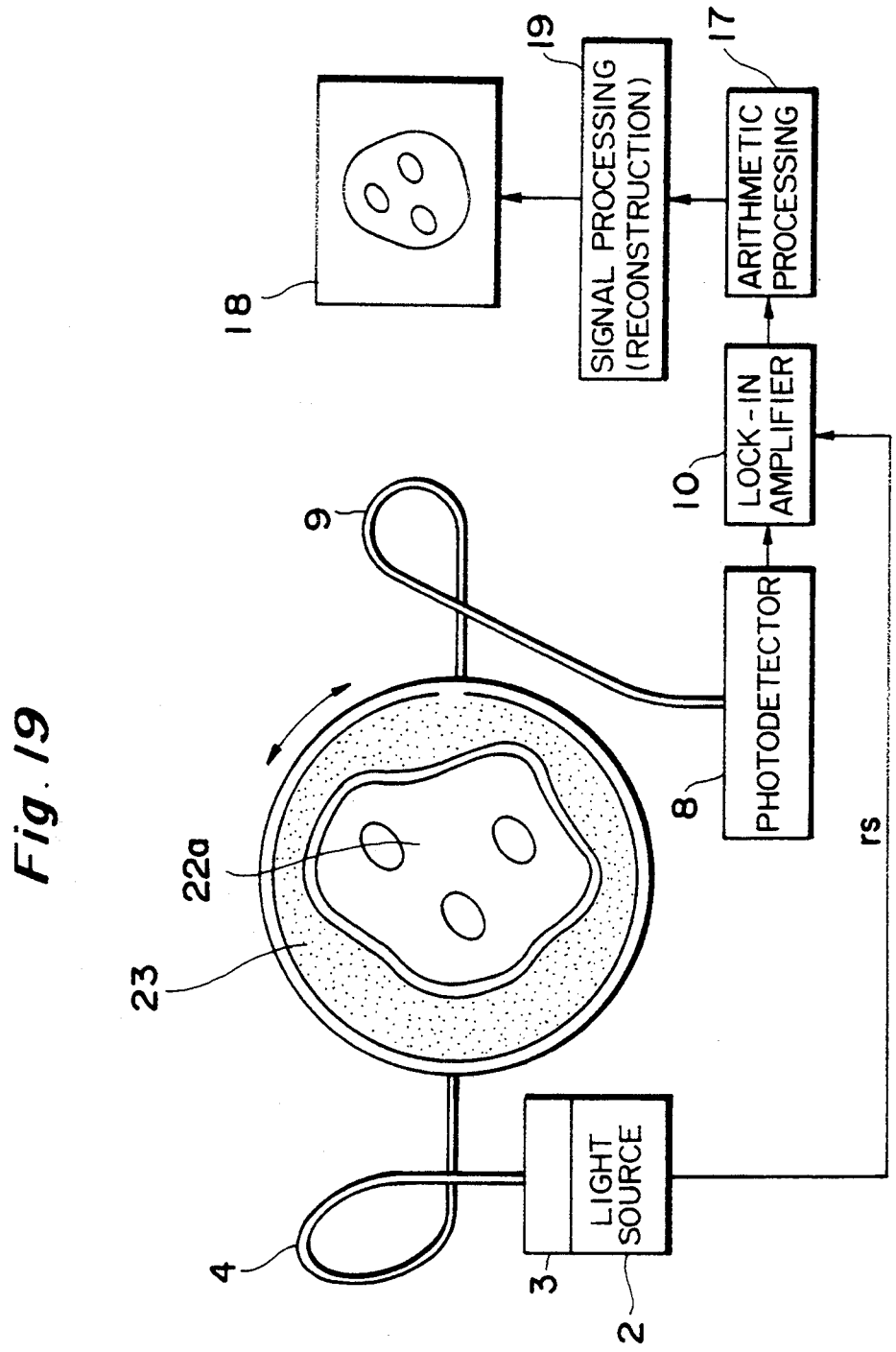
FIG. 19 is a diagram showing an arrangement of the third embodiment.

FIG. 19 shows an arrangement of an apparatus obtaining a tomogram of absorption information in a scattering medium according to the third embodiment. In the first and second embodiments, light transmitted through each portion along the optical axis is detected. In the third embodiment, an object to be measured or a pair of light source 2 and photodetector 8 are rotated, or rotated and translated so that the direction of optical axis for detecting this transmitted light is set for each of all directions. The resultant signal is processed to reconstruct a tomogram as in CT.

Modulated light emitted from a light source 2 is selected by a wavelength selector 3 and is incident on an object 22a to be measured, surrounded by an interface material 23, through an optical fiber 4. The interface material 23 has the optical properties as described above and is filled in a thin film bag having a low reflectance. Light incident on the bag filled with the interface material is less reflected at on the surface of the bag. If the outer and inner surfaces of the thin film are constituted by rough surfaces, the incident light has light components propagating in all directions. In this case, the modulated light propagates through the interface material 23 and the object 22a and reaches the opposite side where an optical guide 9 is located. So that output light is incident on the photodetector 8 through this optical guide 9. The interior of the bag filled with the interface at positions except for the portions around the opening of the optical guide 9 and the light incident aperture is preferably constituted by a light-absorbing medium. Light reflection on the inner surface of the bag can be eliminated, and accurate measurement can be performed.

The object 22a is rotated relative to the light source optical fiber, the photodetection guide, the interface material, and its vessel. The outer shape of the interface vessel (bag) is circular, but the inner side must have a shape conforming to the shape of the object to be measured. At the same time, even if the object to be measured is rotated, a space formed between the object and the bag must always be filled by the bag filled with the interface material. Such a structure can be obtained by a scheme having one vessel which surrounds the object to be measured 22a, as shown in FIG. 19, or a scheme for preparing two vessels on the light incident and exit sides. In either scheme, the interface material in the bag is brought into tight contact with the light incident and light-receiving apertures by the effect of gravity or a pressure. At the same time, the inner side of the interface material 23 is brought into contact with the object to be measured 22a.

FIG. 20 shows a case using two interface vessels. The interface vessels are soft bags variously surface-treated, as shown in FIG. 20. Each bag contains water with a scattering medium such as fine particles and the light. The surfaces of the bags are brought into contact by the gravity or a pressure with the inlet and outlet ports for the light and the object to be measured 22a. The outer shape of the object to be measured 22a is assumed to have a relatively smooth curve. If the object to be measured may be dipped in a liquid, the vessels brought into contact with the object to be measured 22a can be omitted, and the object to be measured 22a can be directly dipped in the liquid.

An optical signal obtained as described above is processed as in the first and second embodiments. Image reconstruction as in X-ray CT is performed by a signal processing unit 19 using the absorption information in all optical axes extending the object to be measured. A tomogram is obtained on an image display recording unit 18. The same operation can be performed in a system in FIG. 20 in which the object to be measured 22a is rotated, and the remaining components are stationary.

More specifically, FIG. 20 shows an arrangement including optical fiber 4, interface material 23, vessel 221 and optical guide 9, where treatments being performed include scattering surface treatment SSC, and anti-reflection treatment ART and anti-reflection absorption treatment ARAT.

Tomograms obtained in this embodiment represent the distribution of a ratio of an absorption coefficient to a reference value, the distribution of a degree of saturation of hemoglobins, and the like.

(4) Fourth Embodiment

The fourth embodiment uses a plurality of photodetectors. Equations (1.1) to (1.4) described above are established in either direction if light propagates in the scattering medium. The arrangement (FIG. 12) using a plurality of photodetectors can be obtained. With this arrangement, the distribution of transmittances like a panoramic image is obtained by viewing an object from the light incident point in a wide range. This arrangement makes it possible to shorten the measurement time as compared with a scheme in which one photodetector is moved from $D_1$ to $D_5$. When the pitch between the adjacent photodetectors is large, the photodetector array may be rotated and scanned about the light incident point to obtain an image having a higher sampling density. A plurality of optical fibers having the same length may be located at the positions of the photodetectors, and opposite ends of the optical fibers may be connected to the plurality of photodetectors or the photodetector array or the like.

(5) Fifth Embodiment

In the fifth embodiment, the arrangement described with reference to the fourth embodiment is added to the tomographic imaging apparatus of the third embodiment. This arrangement is identical to a fan-beam scheme in X-ray CT, so that a tomogram can be obtained at a higher speed.

(6) Sixth Embodiment

FIG. 21 shows an arrangement using an optical heterodyne method according to the sixth embodiment. When the frequency of a modulated wave is high (e.g., 100 MHz or more), the optical heterodyne method is used in place of the heterodyne type lock-in amplifier 211 (FIG. 10C) described with reference to the first embodiment. Detection light D1 containing a signal of a modulated frequency component f is mixed by mixer 215 with modulated light (modulation frequency $(f-f_b)$) from another light source 215 (local oscillator), so that their beat signal (frequency $f_b$) is generated. This beat signal is photodetected by photodetector 214 and the envelope of photodetected signal is then detected by a detector circuit 213. The envelope signal has the frequency $f_b$, which is then input to the lock-in amplifier or the like. In this case, the modulation frequency $(f-f_b)$ of the local oscillator is selected to establish $f \approx 1$ MHz to 1 GHz and $f_b \approx 1$ KHz to 1 MHz.

As has been described above, according to an apparatus for measuring absorption information in a scattering medium and a method therefor, light utilization efficiency can be improved, and absorption information (e.g., an absorption efficiency ratio and a degree of saturation of hemoglobins), their spatial distributions, and the distribution within a slice can be highly precisely measured. In the absorption information measurement apparatus utilizing the method of the present invention, light utilization efficiency can be improved, and measurement precision can be essentially improved in accordance with the principle of detection of parameters such as a phase. Imaging and tomographic measurements a human head and body can be performed. The present invention, therefore, is a remarkable invention capable of measuring absorption information in the scattering medium using light or imaging the absorption information, thereby providing great advantages in the society.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for measuring absorption information in a scattering medium, comprising
   light-emitting means for emitting modulated light having a predetermined wavelength,
   light-incident means for forming the modulated light having the predetermined wavelength into a spot and causing the spot to be incident on the scattering medium,
   photodetecting means for photodetecting the modulated light, changed during propagation in the scattering medium, through an opening located near an outer surface of the scattering medium, signal extracting means for extracting a signal of one predetermined frequency component constituting the modulated light from signals photodetected by said photodetecting means, parameter detecting means for comparing the signal extracted by the signal extracting means with the signal of the predetermined frequency component of the modulated light to be incident on the scattering medium and detecting a predetermined parameter associated with propagation of a photon density wave having the predetermined frequency component in the scattering medium and absorption of the light of the predetermined wavelength constituting the photon density wave having the predetermined frequency component, first arithmetic processing means for calculating first absorption information associated with an absorptive constituent in the scattering medium, utilizing a relationship between the predetermined parameter and an absorption coefficient obtained when the photon density wave having the predetermined frequency component propagates in the scattering medium, and second arithmetic processing means for calculating second absorption information associated with the absorption coefficient in the scattering medium, on the basis of a plurality of first absorption information obtained by the first arithmetic processing means.

2. An apparatus for measuring absorption information in a scattering medium according to claim 1, wherein the modulated light emitted by the light-emitting means has at least two wavelengths that are different from each other, the absorptive constituent in the scattering medium having a different absorption coefficient with respect to each of the wavelengths of the modulated light, and the second arithmetic processing means calculates the second absorption information with respect to a concentration of a specific absorptive constituent in the scattering medium based on the plurality of first absorption information obtained by said first arithmetic processing means for each of the wavelengths of the modulated light.

3. An apparatus for measuring absorption information in a scattering medium according to claim 1, wherein the second arithmetic processing means calculates second absorption information corresponding to a time change in a specific absorptive constituent in the scattering medium at least two different times based on the plurality of first absorption information obtained by the first arithmetic processing means.

4. An apparatus for measuring absorption information in a scattering medium according to any one of claims 1 to 3, further comprising:

scanning means for scanning the scattering medium on which the spot-like modulated light from the light-incident means is incident, and arithmetic processing display means for generating image data by arithmetically processing position signals corresponding to scanning records of the scanning means and the second absorption information from the second arithmetic processing means, and for displaying the image data.

5. An apparatus for measuring absorption information in a scattering medium according to claim 4, wherein the predetermined parameter is a phase difference between the signal extracted by the signal extracting means and the signal having the predetermined frequency component of the modulated light to be incident on the scattering medium.

6. An apparatus for measuring absorption information in a scattering medium according to claim 5, wherein the first arithmetic processing means is further for calculating first absorption information associated with an absorptive constituent in the scattering medium based on the relationship between the predetermined parameter and the absorption coefficient, the relationship being so defined that the absorption coefficient of the absorptive constituent in the scattering medium is in inverse proportion to a square of the phase difference.

7. An apparatus for measuring absorption information in a scattering medium according to claim 4, wherein the predetermined parameter is an amplitude of the signal extracted by the signal extracting means.

8. An apparatus for measuring absorption information in a scattering medium according to any one of claims 1 to 3, further comprising displacing means for displacing an incident position of the spot-like modulated light from the light-incident means on the scattering medium along a slice of the scattering medium, and image constructing means for reconstructing a tomogram of the scattering medium based on basis of a displacement signal corresponding to a displacement by the displacing means and the second absorption information obtained by the second arithmetic processing means.

9. An apparatus for measuring absorption information in a scattering medium according to claim 8, wherein the predetermined parameter is a phase difference between the signal extracted by the signal extracting means and the signal having the predetermined frequency component of the modulated light to be incident on the scattering medium.

10. An apparatus for measuring absorption information in a scattering medium according to claim 9, wherein the first arithmetic processing means is further for calculating first absorption information associated with an absorptive constituent in the scattering medium based on the relationship between the predetermined parameter and the absorption coefficient, the relationship being so defined that the absorption coefficient of the absorptive constituent in the scattering medium is in inverse proportion to a square of the phase difference.

11. An apparatus for measuring absorption information in a scattering medium according to claim 8, wherein the predetermined parameter is an amplitude of the signal extracted by the signal extracting means.

12. An apparatus for measuring absorption information in a scattering medium according to any one of claims 1 to 3, wherein the photodetecting means comprises a plurality of photodetectors for independently detecting the modulated light components propagating through the scattering medium.

13. An apparatus for measuring absorption information in a scattering medium according to claim 12, wherein the predetermined parameter is a phase difference between the signal extracted by the signal extracting means and the signal having the predetermined frequency component of the modulated light to be incident on the scattering medium.

14. An apparatus for measuring absorption information in a scattering medium according to claim 13, wherein the first arithmetic processing means is further for calculating first absorption information associated with an absorptive constituent in the scattering medium based on the relationship between the predetermined parameter and the absorption coefficient, the relationship being so defined that the absorption coefficient of the absorptive constituent in the scattering medium is in inverse proportion to a square of the phase difference.

15. An apparatus for measuring absorption information in a scattering medium according to claim 12, wherein the predetermined parameter is an amplitude of the signal extracted by the signal extracting means.

16. An apparatus for measuring absorption information in a scattering medium according to any one of claims 1 to 3, further comprising displacing means for displacing an incident position of the spot-like modulated light from the light-incident means on the scattering medium along a slice of the scattering medium and displacing said plurality of photodetectors in synchronism with a displacement of the incident position, and image constructing means for reconstructing a tomogram of the scattering medium on the basis of a displacement signal corresponding to the displacement by the displacing means and the second absorption information obtained by the second arithmetic processing means.

17. An apparatus for measuring absorption information in a scattering medium according to claim 16, wherein the predetermined parameter is a phase difference between the signal extracted by the signal extracting means and the signal having the predetermined frequency component of the modulated light to be incident on the scattering medium.

18. An apparatus for measuring absorption information in a scattering medium according to claim 17, wherein the first arithmetic processing means is further for calculating first absorption information associated with an absorptive constituent in the scattering medium based on the relationship between the predetermined parameter and the absorption coefficient, the relationship being so defined that the absorption coefficient of the absorptive constituent in the scattering medium is in inverse proportion to a square of the phase difference.

19. An apparatus for measuring absorption information in a scattering medium according to claim 16, wherein the predetermined parameter is an amplitude of the signal extracted by the signal extracting means.

20. An apparatus for measuring absorption information in a scattering medium according to any one of claims 1 to 3, wherein the predetermined parameter is a phase difference between the signal extracted by the signal extracting means and the signal having the predetermined frequency component of the modulated light to be incident on the scattering medium.

21. An apparatus for measuring absorption information in a scattering medium according to claim 20, wherein the first arithmetic processing means is further for calculating first absorption information associated with an absorptive constituent in the scattering medium based on the relationship between the predetermined parameter and the absorption coefficient, the relationship being so defined that the absorption coefficient of the absorptive constituent in the scattering medium is in inverse proportion to a square of the phase difference.

22. An apparatus for measuring absorption information in a scattering medium according to any one of claims 1 to 3, wherein the predetermined parameter is an amplitude of the signal extracted by the signal extracting means.

23. A method of measuring absorption information in a scattering medium, comprising
the first step of emitting modulated light having a predetermined wavelength,
the second step of forming the modulated light having the predetermined wavelength light into a spot and causing the spot to be incident on the scattering medium,
the third step of photodetecting the modulated light, changed during propagation in the scattering medium, through an opening located near an outer surface of the scattering medium,
the fourth step of extracting a signal of one predetermined frequency component constituting the modulated light from signals photodetected in the third step,
the fifth step of comparing the signal extracted in the fourth step with the signal of the predetermined frequency component of the modulated light to be incident on the scattering medium and detecting a predetermined parameter associated with propagation of a photon density wave having the predetermined frequency component in the scattering medium and absorption of the light of the predetermined wavelength constituting the photon density wave having the predetermined frequency component,
the sixth step of calculating first absorption information associated with an absorptive constituent in the scattering medium, utilizing a relationship between the predetermined parameter and an absorption coefficient obtained when the photon density wave having the predetermined frequency component propagates in the scattering medium, and
the seventh step of calculating second absorption information associated with the absorption coefficient in the scattering medium, on the basis of a plurality of first absorption information obtained in the sixth step.

24. A method of measuring absorption information in a scattering medium according to claim 23, wherein
the modulated light emitted in the first step has at least two wavelengths that are different from each other, the absorptive constituent in the scattering medium having a different absorption coefficient with respect to each of the wavelengths of the modulated light, and
the second absorption information is calculated with respect to a concentration of a specific absorptive constituent in the scattering medium on the basis of the plurality of first absorption information obtained in the sixth step for each of the wavelengths of the modulated light.

25. A method of measuring absorption information in a scattering medium according to claim 23, further comprising calculating the second absorption information corresponding to a time change in a specific absorptive constituent in the scattering medium at least two different times in the seventh step based on the plurality of first absorption information obtained in the sixth step.

26. A method of measuring absorption information in a scattering medium according to any one of claims 23 to 25, wherein the predetermined parameter is a phase difference between the signal extracted by the signal extracting means and the signal having the predetermined frequency component of the modulated light to be incident on the scattering medium.

27. A method of measuring absorption information a scattering medium according to claim 26, wherein the relationship between the predetermined parameter and the absorption coefficient is so defined that the absorption coefficient of the absorptive constituent in the scattering medium is an inverse proportion to a square of the phase difference.

* * * * *